United States Patent
Seo

(10) Patent No.: US 9,532,839 B2
(45) Date of Patent: Jan. 3, 2017

(54) SURGICAL ROBOT SYSTEM AND METHOD OF CONTROLLING THE SAME

(71) Applicant: Samsung Electronics Co., Ltd., Suwon-Si, Gyeonggi-Do (KR)

(72) Inventor: Kee Hong Seo, Seoul (KR)

(73) Assignee: Samsung Electronics Co., Ltd., Gyeonggi-do (KR)

(*) Notice: Subject to any disclaimer, the term of this patent is extended or adjusted under 35 U.S.C. 154(b) by 155 days.

(21) Appl. No.: 14/187,803

(22) Filed: Feb. 24, 2014

(65) Prior Publication Data

US 2015/0045812 A1    Feb. 12, 2015

(30) Foreign Application Priority Data

Aug. 6, 2013   (KR) ........................ 10-2013-0093016

(51) Int. Cl.
*G06F 19/00*      (2011.01)
*A61B 19/00*      (2006.01)

(52) U.S. Cl.
CPC ........... *A61B 19/2203* (2013.01); *A61B 34/30* (2016.02); *A61B 34/37* (2016.02); *A61B 34/77* (2016.02)

(58) Field of Classification Search
CPC ................... A61B 19/2203; A61B 2019/2223; A61B 2019/2296; A61B 2019/464
USPC ........ 700/245, 257, 260; 606/118, 130, 139; 901/47; 318/568.11, 568.1
See application file for complete search history.

(56) References Cited

U.S. PATENT DOCUMENTS

| | | | | |
|---|---|---|---|---|
| 6,594,552 | B1* | 7/2003 | Gerbi ..................... | A61B 19/22 318/568.11 |
| 6,684,129 | B2* | 1/2004 | Salisbury, Jr. ......... | A61B 19/22 128/897 |
| 6,728,599 | B2* | 4/2004 | Wang ..................... | A61B 19/22 128/897 |
| 6,839,612 | B2* | 1/2005 | Sanchez ............. | A61B 19/2203 318/568.11 |
| 7,155,316 | B2* | 12/2006 | Sutherland ............. | A61B 19/22 318/568.11 |
| 7,248,944 | B2* | 7/2007 | Green ................ | A61B 1/00193 348/E13.014 |
| 7,386,365 | B2* | 6/2008 | Nixon .................... | A61B 19/22 606/139 |
| 8,029,516 | B2 | 10/2011 | Mohr et al. | |
| 9,060,796 | B2* | 6/2015 | Seo .................... | A61B 19/2203 |

(Continued)

OTHER PUBLICATIONS

Ikuta et al. Hyper Redundant Miniature Manipulator 'Hyper Finger for Remote Minimally Invasive Surgey in Deep Area, 2003, IEEE, p. 1098-1102.*

(Continued)

*Primary Examiner* — McDieunel Marc
(74) *Attorney, Agent, or Firm* — Harness, Dickey & Pierce, P.L.C.

(57) ABSTRACT

A surgical robot system includes a slave device having a surgical instrument; and a master device configured to transmit a control signal to the surgical instrument. The slave device includes a guide tube to which the surgical instrument is coupled; and a controller operating the surgical instrument in response to the control signal transmitted from the master device, and operate the guide tube so as to move the surgical instrument to a target position if the target position of the surgical instrument according to the control signal corresponds to a position out of a range of a current working space for the surgical instrument.

20 Claims, 14 Drawing Sheets

(56) References Cited

U.S. PATENT DOCUMENTS

| | | |
|---|---|---|
| 9,226,796 B2 * | 1/2016 | Bowling ............ A61B 19/2203 |
| 2008/0064921 A1 | 3/2008 | Larkin et al. |
| 2008/0071291 A1 | 3/2008 | Duval et al. |
| 2010/0274087 A1 * | 10/2010 | Diolaiti ............. A61B 1/00087 |
| | | 600/118 |
| 2010/0275718 A1 | 11/2010 | Stuart et al. |
| 2011/0230894 A1 | 9/2011 | Simaan et al. |
| 2014/0276940 A1 * | 9/2014 | Seo .................... A61B 19/2203 |
| | | 606/130 |
| 2015/0018841 A1 * | 1/2015 | Seo .................... A61B 19/2203 |
| | | 606/130 |
| 2015/0066051 A1 * | 3/2015 | Kwon ....................... B25J 3/04 |
| | | 606/130 |

OTHER PUBLICATIONS

Mack, Minimally Invasive and Robotic Surgery, 2001, Internet. p. 568-572.*

* cited by examiner

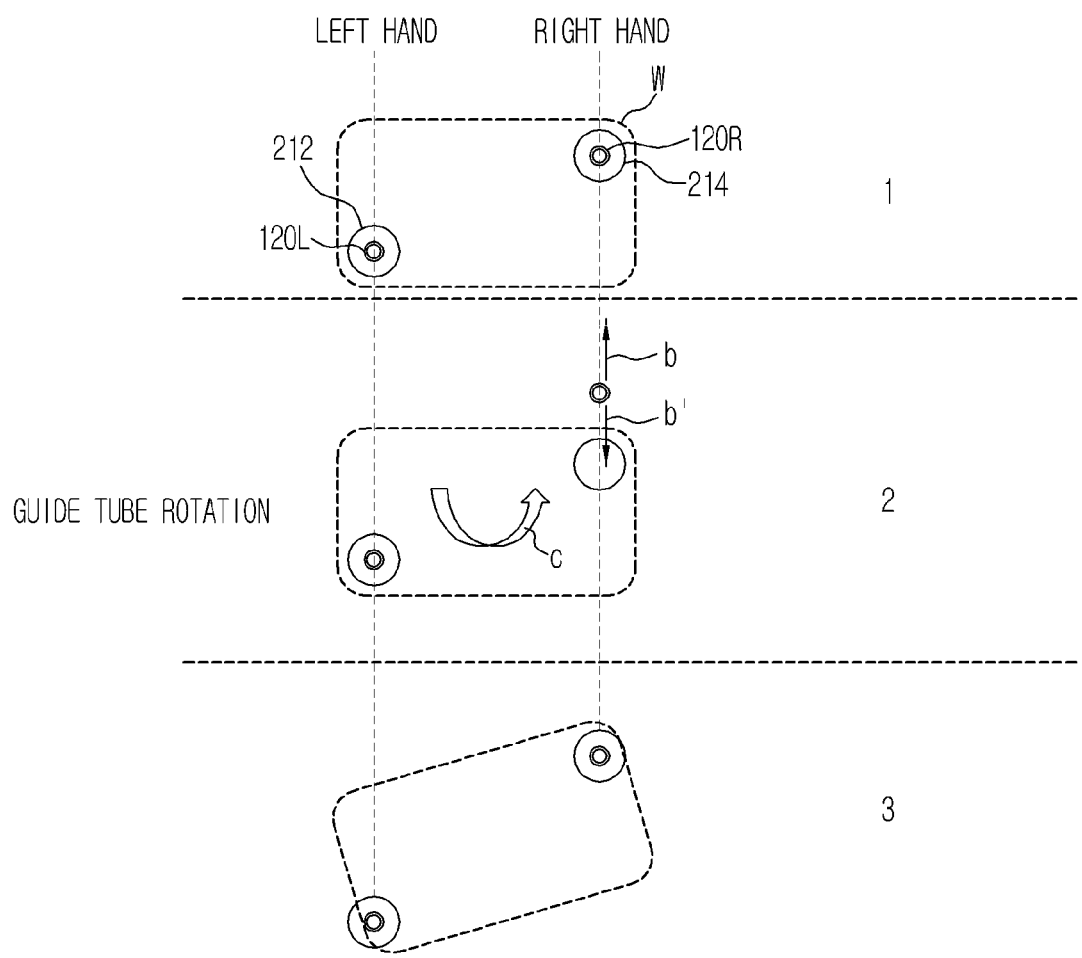

SURGICAL ROBOT SYSTEM AND METHOD OF CONTROLLING THE SAME

CROSS-REFERENCE TO RELATED APPLICATION

This application claims the benefit of Korean Patent Application No. 10-2013-0093016, filed on Aug. 6, 2013 in the Korean Intellectual Property Office, the disclosure of which is incorporated herein by reference.

BACKGROUND

1. Field

Example embodiments relate to a surgical robot system and a method of controlling the same, and more particularly, to a surgical robot system that is capable of extending a limited working space for surgical instruments and a method of controlling the same.

2. Description of the Related Art

In laparotomy, a large slit is opened in a part (for example, an abdominal part) of the human body. In contrast, minimal invasive surgery is a surgical method, whereby at least one slit hole (or an invasive hole) having a size of 0.5 to 1.5 cm is formed in the human body, an endoscope and various surgical instruments are inserted through the slit hole, and then a surgeon may perform the surgical method by watching an image.

In minimal invasive surgery, less pain after surgery, an early recovery of enterokinesia, and an early intake of food may be possible as compared to laparotomy. Further, a relatively short hospitalization period, a relatively quick return to a normal state, and a relatively narrow slit range are obtained compared to laparotomy. Thus, minimal invasive surgery has high beauty treatment effects. Owing to these advantages, minimal invasive surgery use in cholecystectomy, prostate cancer surgery, and hernia repair and other fields is gradually expanding.

In general, surgical robots used in minimal invasive surgery may include a master device and a slave device. The master device generates a control signal through a surgeon's manipulation and transmits the control signal to the slave device. The slave device receives the control signal from the master device and applies manipulation required for surgery to a patient. The master device and the slave device are integrated with each other or are individually configured and thus are disposed in an operating room so as to perform an operation.

These surgical robots are largely classified into multi-port surgical robots that perform an operation by forming several invasive holes in the body of the patient and by inserting a surgical instrument into each invasive hole and single port surgical robots that perform an operation by forming one invasive hole in the body of the patient and by inserting a plurality of surgical instruments into one invasive hole at one time.

The single port surgical robots may insert a plurality of surgical instruments into the body of the patient through one guide tube inserted into the invasive hole. The guide tube and each of the plurality of surgical instruments have an individual degree of freedom. Also, a working space for the plurality of surgical instruments inserted into the body of the patient through the guide tube may be limited according to the position and orientation of the surgical instruments.

SUMMARY

Example embodiments provide a surgical robot system that is capable of extending the range of a working space for surgical instruments using a motion of a guide tube having redundancy, and a method of controlling the surgical robot system.

Additional aspects of the example embodiments will be set forth in part in the description which follows and, in part, will be obvious from the description, or may be learned by practice of the example embodiments.

In accordance with one example embodiment, a surgical robot system includes: a slave device having a surgical instrument; and a master device controlling an operation of the surgical instrument, wherein the slave device includes: a guide tube to which the surgical instrument is coupled; and a controller operating the surgical instrument in response to a control signal transmitted from the master device and if a target position of the surgical instrument according to the control signal corresponds to a position out of a range of a current working space for the surgical instrument, operating the guide tube so as to move the surgical instrument to the target position.

In accordance with another example embodiment, a method of controlling a surgical robot system including a slave device having a guide tube to which a surgical instrument is coupled and a master device controlling an operation of the surgical instrument, includes: determining whether a target position of the surgical instrument according to a control signal transmitted from the master device corresponds to a position out of a range of a current working space for the surgical instrument; and as a result of determination, if it is determined that the target position corresponds to the position out of the range of the current working space for the surgical instrument, operating the guide tube so as to move the surgical instrument to the target position.

At least one example embodiment relates to a slave device configured to perform a surgical procedure based on instructions received from a master device.

In at least one embodiment, the slave device includes surgical instruments configured to act on a patient through a surgical port therein; a guide tube configured to support the surgical instruments and allow the surgical instruments to move within a radius around the guide tube defining a working space; and a controller configured to, reposition the surgical instruments to a target position in response to control signals received from the master device; and reposition the guide tube, if the control signals indicate that the target position of the surgical instruments is outside of the working space of the guide tube.

In at least one embodiment, if the surgical instruments include at least two surgical instruments and the control signal indicates that a spread between the target positions of the at least two surgical instruments can fit within the working space, then the controller is configured to, reposition the guide tube such that the target positions of the at least two surgical instruments are within a new working space, and reposition the surgical instruments without moving the guide tube such that the surgical instruments are repositioned to their associated target positions.

In at least one embodiment, if the surgical instruments include at least two surgical instruments and the control signal indicates that the at least two surgical instruments have a target positions outside of the working space, then the controller is configured to, reposition the guide tube to a new working space in such a way that a deficiency between an actual position of the at least two surgical instruments and the target positions is minimized, and transmit a feedback signal to the master device instructing the master device to inform an operator that the guide tube is unable to be repositioned into a working space that includes the target positions of the at least two surgical instruments.

In at least one embodiment, the controller is configured to minimize the deficiency by minimizing a vector sum of the target positions and current positions of each of the at least two surgical instruments.

In at least one embodiment, the master device informs the operator that the guide tube is unable to be repositioned within the working space by instructing a driving unit to drive handles of the master device in a direction opposite a direction that an operator of the handles applies a force thereto.

BRIEF DESCRIPTION OF THE DRAWINGS

These and/or other aspects of the embodiments will become apparent and more readily appreciated from the following description of the example embodiments, taken in conjunction with the accompanying drawings of which:

FIG. 14 illustrates an example of changing a working space according to a rotational motion of the guide tube.

DETAILED DESCRIPTION

Figure 1:
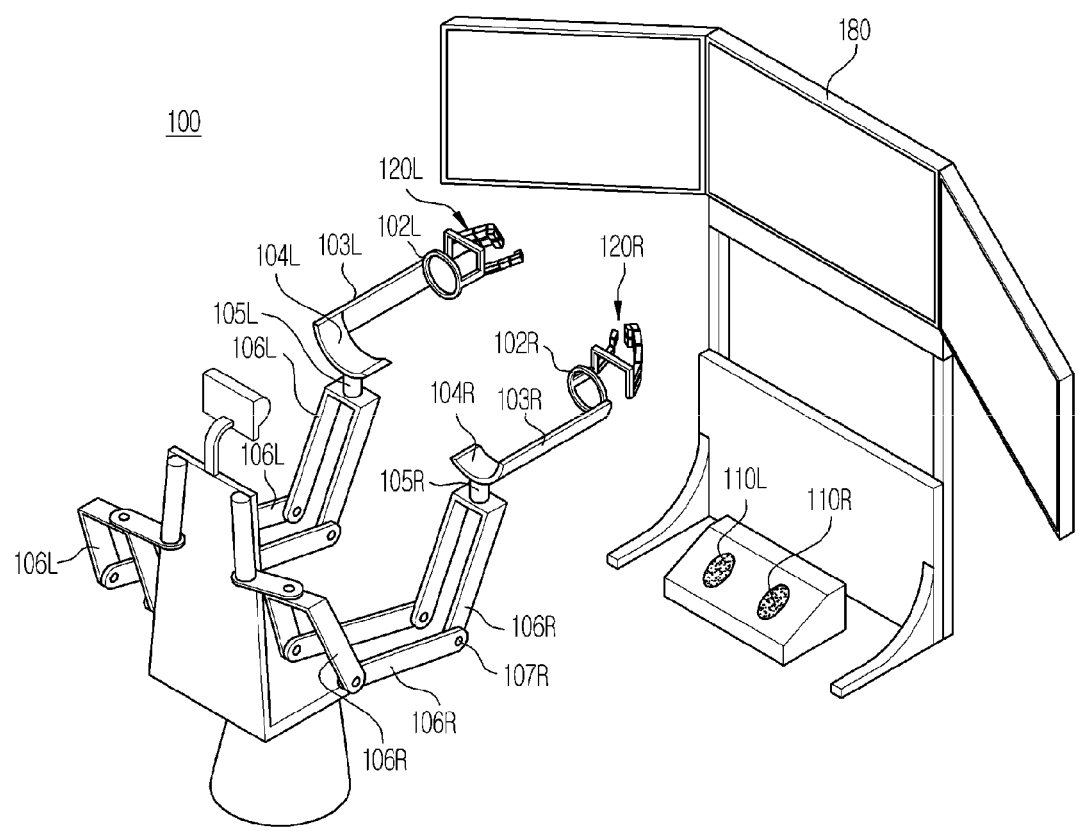
FIG. 1 illustrates the exterior of a master device of a surgical robot system in accordance with an example embodiment.

Purposes, particular advantages, and new features of the embodiments will be more apparent from the following detailed description and example embodiments associated with the attached drawings. When adding reference numerals to elements of the drawings in the specification, it should be noted that like reference numerals if possible are used for like elements even though like elements are show in different drawings. Also, in the description, if it is determined that a detailed description of commonly-used technologies or structures may unnecessarily obscure the subject matter, the detailed description will be omitted. It will be understood that although the terms first and second are used herein to describe various elements, these elements should not be limited by these terms. These terms are only used to distinguish one element from another element.

Reference will now be made in detail to example embodiments which are illustrated in the accompanying drawings, wherein like reference numerals refer to like elements throughout.

Although a single port surgical robot (hereinafter, referred to as a 'surgical robot system') will be described, this is just one example, and example embodiments are not limited thereto. For example, example embodiments may be applied to the field of all devices having a shape in which several tools are diverged from one manipulator, in addition to the field of all robots including various industrial service robots, such as a rescue robot for searching a survivor in a disaster area, a medical robot, such as an endoscope or Active Catheter, a military robot, a robot that performs various works in the universe, a hazardous material-handling robot, and a pipe cleaning robot.

Example embodiments will now be described more fully with reference to the accompanying drawings, in which some example embodiments are shown. In the drawings, the thicknesses of layers and regions are exaggerated for clarity. Like reference numerals in the drawings denote like elements.

Detailed illustrative embodiments are disclosed herein. However, specific structural and functional details disclosed herein are merely representative for purposes of describing example embodiments. Example embodiments may be embodied in many alternate forms and should not be construed as limited to only those set forth herein.

It should be understood, however, that there is no intent to limit this disclosure to the particular example embodiments disclosed. On the contrary, example embodiments are to cover all modifications, equivalents, and alternatives falling within the scope of the example embodiments. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of this disclosure. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Various example embodiments will now be described more fully with reference to the accompanying drawings in which some example embodiments are shown. In the drawings, the thicknesses of layers and regions are exaggerated for clarity.

Figure 2:
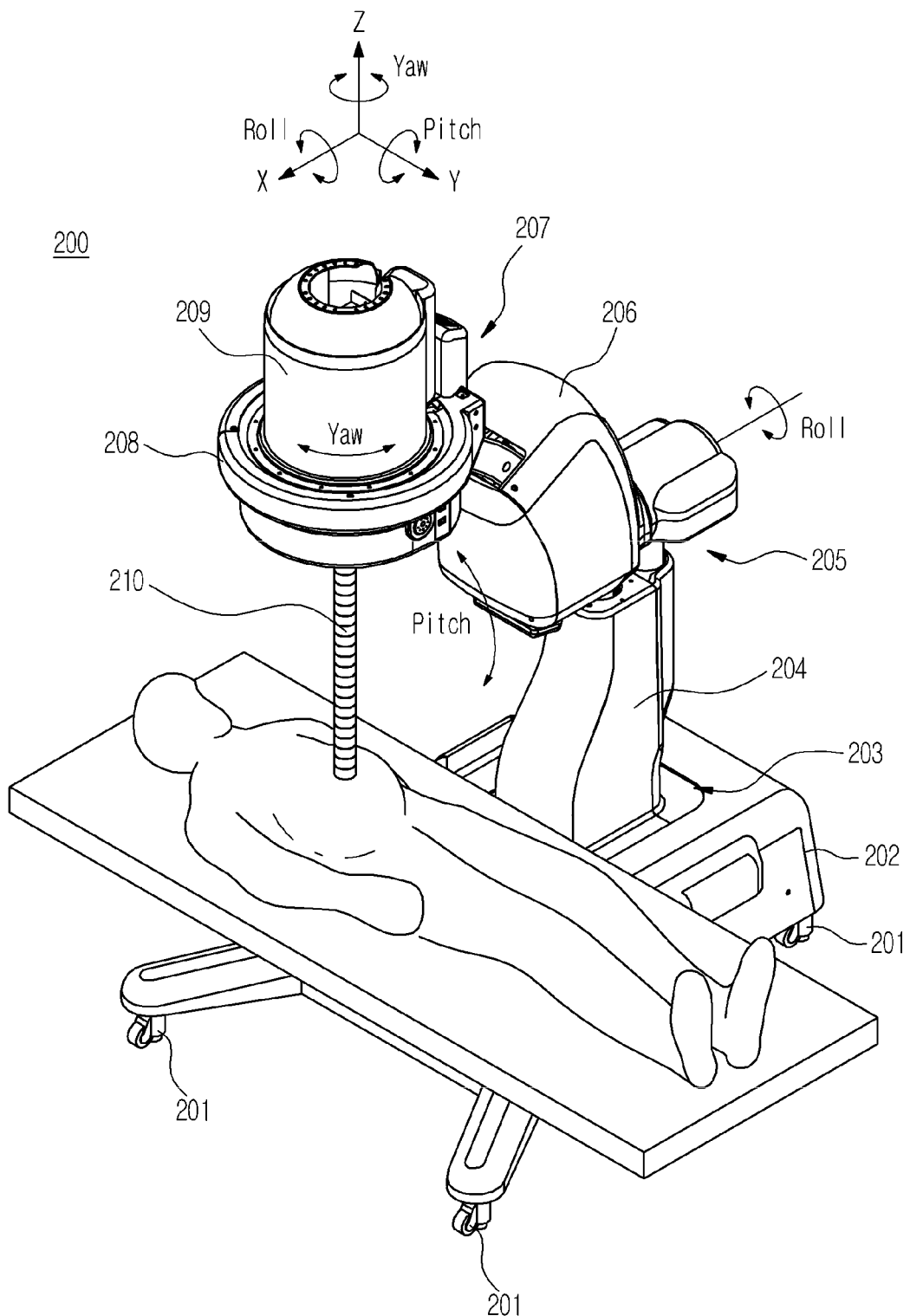
FIG. 2 illustrates the exterior of a slave device of the surgical robot system illustrated in FIG. 1.

FIG. 1 illustrates the exterior of a master device of a surgical robot system in accordance with an example embodiment, and FIG. 2 illustrates the exterior of a slave device of the surgical robot system illustrated in FIG. 1.

Referring to FIGS. 1 and 2, the surgical robot system may include a slave device 200 that performs an operation on a patient who lies on an operating table and a master device 100 that remotely controls the slave device 200 through manipulator's (for example, surgeon's) manipulation. One or more assistants who assist a manipulator may stand at the side of the patient.

Here, assisting the manipulator may mean manipulating the surgical instruments, for example, by replacing surgical instruments used in the operating work. However, example embodiments are not limited thereto. The number of robot arms 210 of the slave device 200 and the number of surgical instruments mounted at one time may be limited. Since the number of invasive holes may be limited (for example, a single invasive hole in the case of single port surgery), the number of surgical instruments that may be inserted into an abdominal cavity of the patient may be limited.

Thus, when the surgical instruments need to be replaced while the operating work is performed, the manipulator may instruct the assistant who stands at the side of the patient to replace the surgical instruments, and the assistant may perform a surgical instrument replacing work, such as taking out the surgical instruments inserted into the abdominal cavity of the patient and replacing the surgical instruments with other surgical instruments and inserting the other surgical instruments according to the manipulator's instruction.

Although the master device 100 and the slave device 200 may be configured as physically individual devices, example embodiments are not limited thereto, and the master device 100 and the slave device 200 may also be configured as an integrated type in which they are integrated with each other.

The surgical robot system mainly includes the master device 100 and the slave device 200. The master device 100 is a device that remotely controls the slave device 200. The master device 100 generates a control signal according to the manipulator's manipulation and transmits the generated control signal to the slave device 200. The slave device 200 receives the control signal from the master device 100 and operates according to the received control signal.

FIG. 1 illustrates the exterior of a master device of a surgical robot system in accordance with an example embodiment.

Referring to FIG. 1, the master device 100 may include input units 110L, 110R, 120L, and 120R, and a display unit 180.

The input units 110L, 110R, 120L, and 120R receive instructions to remotely manipulate an operation of a slave device 200 (with reference to FIG. 2) from the manipulator (for example, the surgeon). In FIG. 1, two clutch pedals 110L and 110R and two handle units 120L and 120R are provided at the input units 110L, 110R, 120L, and 120R. However, example embodiments are not limited thereto, and a switch, a button, a voice recognition device, and the like may be further provided.

For example, the clutch pedals 110L and 110R may be used to convert an operating mode of the surgical robot system. For example, when the left clutch pedal 110L is manipulated, a guide tube manipulation mode may be executed, and when the right clutch pedal 110R is manipulated, a surgical instrument manipulation mode may be executed. In this case, when the guide tube manipulation mode is executed, the manipulator manipulates the handle units 120L and 120R so as to change a position and orientation of a guide tube 210 (with reference to FIG. 2). Also, when the surgical instrument manipulation mode is executed, the manipulator manipulates the handle units 120L and 120R so as to change positions, orientations, and operations of surgical instruments 212, 214 (with reference to FIG. 3).

Figure 3:
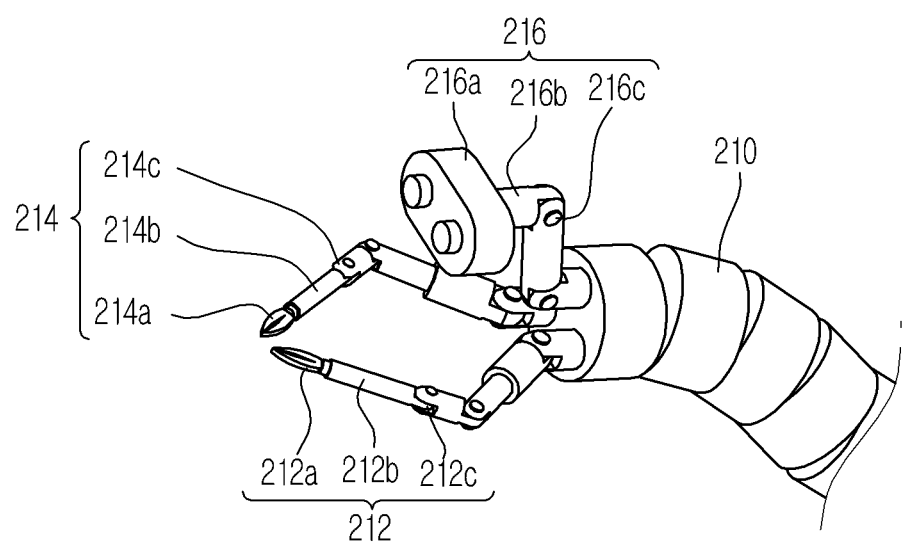
FIG. 3 illustrates surgical instruments unfolded through a guide tube.

The handle units 120L and 120R are used to control motions of robot arms 203 to 208 disposed at the slave device 200, the guide tube 210, the surgical instruments 212 and 214, and an endoscope 216 (with reference to FIGS. 2 and 3). The handle units 120L and 120R may be implemented with haptic devices; however, example embodiments are not limited thereto. The handle units 120L and 120R may include at least one multi-joint robot finger. In this case, a multi-joint robot finger may be disposed in a similar shape to a human hand. In FIG. 1, three multi-joint robot fingers are provided in a shape in which they are provided in positions corresponding to the thumb, the index finger, and the middle finger of the human hand. In FIG. 1, three multi-joint robot fingers are provided at each of the handle units 120L and 120R. However, the number of multi-joint robot fingers or their positions are not limited thereto.

Each multi-joint robot finger may include a plurality of links and a plurality of joints. Here, 'joint' may mean a connection unit between links and may have at least one degree of freedom (DOF). In this case, the degree of freedom (DOF) is a degree of freedom in forward kinematics or inverse kinematics. The DOF of kinematics is the number of independent motions of a mechanism, or the number of variables for determining independent motions at relative positions between links. For example, an object in a three-dimensional space including the x-axis, the y-axis, and the z-axis has at least one of three degrees of freedom (3 DOF) (position at each axis) for determining a spatial position of the object and three degrees of freedom (3 DOF) (rotation angle with respect to each axis) for determining a spatial orientation of the object. In detail, when the object is movable along each axis and is rotatable around each axis, the object may have six degrees of freedom (6 DOF).

A detection unit for detecting information regarding the state of each joint may be provided at each joint of the multi-joint robot finger. In this case, the detection unit may include a position detection unit (see 122 of FIG. 7) for detecting a position of a joint, e.g., a joint angle, and a velocity detection unit (see 124 of FIG. 7) for detecting the velocity of the joint.

A ring-shaped insertion hole, into which an end of a finger of the manipulator may be inserted, may be provided in a front end of the multi-joint robot finger. Thus, when the manipulator moves his/her own finger being inserted into the insertion hole, the multi-joint robot finger may move so as to correspond to the motion of the finger, and the detection unit provided at each joint of the multi-joint robot finger may detect information regarding the state of the moving joint.

In this case, the position and velocity of each joint detected by the position detection unit 122 and the velocity detection unit 124 may be converted into control signals regarding a target position and a target velocity to be followed by each joint of the surgical instruments 212 and 214 of the slave device 200, and the converted control signals may be transmitted to the slave device 200 via a network. Here, the 'network' may be a wired network, a wireless network, or an integrated wired/wireless network.

Hereinafter, for convenience of explanation, the control signals regarding the target position and the target velocity to be followed by each joint of the surgical instruments 212 and 214 described above will be referred to as first operation control signals.

The shape of the handle units 120L and 120R is not limited to the shape of the multi-joint robot finger, as illustrated in FIG. 1, and may be a pencil shape, a stick shape, or the same shape as that of real surgical instruments. Although, in FIG. 1, the left handle unit 120L and the right handle unit 120R have the same shape, example embodiments are not limited thereto. For example, the left handle unit 120L and the right handle unit 120R may also be implemented with different shapes.

Support links 103L and 103R that are mechanically connected to the handle units 120L and 120R may be provided, as illustrated in FIG. 1. The support links 103L and 103R may support a unit of the body of the manipulator from the wrist to the elbow. To this end, the support links 103L and 103R may include wrist support parts 102L and 102R and elbow support parts 104L and 104R. The wrist support parts 102L and 102R may be disposed at a position corresponding to the manipulator's wrist and may have various shapes. For example, in FIG. 1, the wrist support parts 102L and 102R are implemented with a ring shape. The manipulator may enable his/her own hand to pass through the wrist support parts 102L and 102R and then may insert an end of his/her own finger into the insertion hole formed in the front end of the handle units 120L and 120R.

The elbow support parts 104L and 104R may be disposed at a position corresponding to the manipulator's elbow. The elbow support parts 104L and 104R may have a U shape, as illustrated in FIG. 1; however, example embodiments are not limited thereto.

The support links 103L and 103R including the wrist support parts 102L and 102R and the elbow support parts 104L and 104R may be provided such that the manipulator's arm may be kept in a stable state and thus stable manipulation may be performed.

At least one connection link 106L and 106R that mechanically connect the support links 103L and 103R to a chair on which the manipulator sits may be provided. In this case, joints 105L and 105R may be provided between the connection links 106L and 106R and the support links 103L and 103R. Also, a plurality of connection links 106L and 106R may be provided, as illustrated in FIG. 1. In this case, joints 107L and 107R that connect the plurality of connection links 106L and 106R to each other may be provided.

As illustrated in FIG. 1, two handle units 120L and 120R may be mechanically connected to the chair by the support links 103L and 103R and the connection links 106L and 106R. However, example embodiments are not limited thereto. For example, the support links 103L and 103R and the connection links 106L and 106R may be omitted, and instead, a communication unit (not shown) that receives/transmits data from/to a controller (not shown) of the master device 100 via wired or wireless communication may be additionally provided at each of the handle units 120L and 120R.

Figure 4:
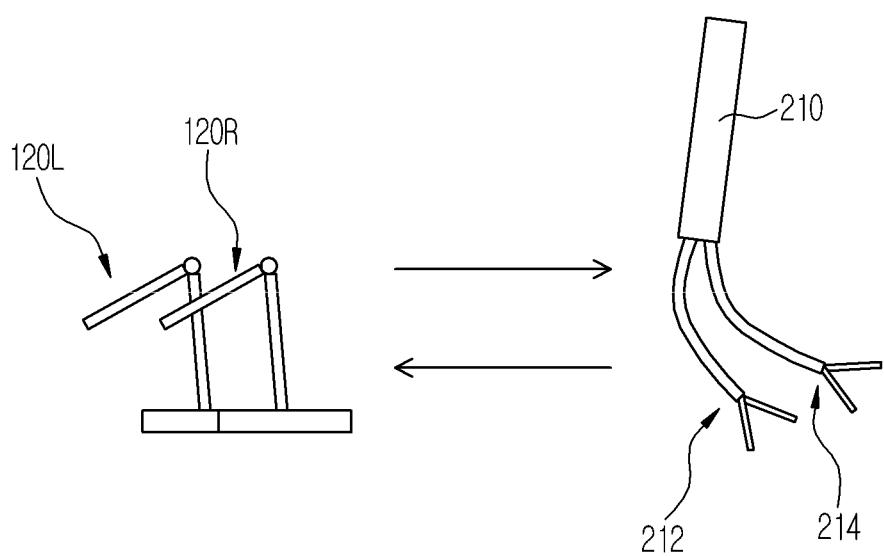
FIG. 4 illustrates an example of the relationship between handle units of the master device and surgical instruments of the slave device.

A manipulation portion of the input unit 110 may be provided with the number corresponding to the number of surgical instruments of the slave device 200; however, example embodiments are not limited thereto. That is, as illustrated in FIG. 4, when the number of surgical instruments 212 and 214 is two, handle units of the master device 100 may also be two handle units 120L and 120R so that the handle units 120L and 120R may control operations of the surgical instruments 212 and 214. However, example embodiments are not limited thereto.

Hereinafter, the case where operations of the surgical instruments 212 and 214 of the slave device 200 are controlled by manipulating the handle units 120L and 120R will be described. However, as described above, a configuration, an operation of which may be controlled by manipulating the handle units 120L and 120R, is not limited to a surgical instrument.

Referring to FIG. 4, the manipulator manipulates two handle units 120L and 120R with both hands, thereby individually controlling operations of two surgical instruments 212 and 214 of the slave device 200. Hereinafter, for convenience of explanation, the handle unit 120L of two handle units 120L and 120R is referred to as a first handle unit 120L, the handle unit 120R of two handle units 120L and 120R is referred to as a second handle unit 120R, a first one of the surgical instruments 212 and 214 that is controlled by manipulating the first handle unit 120L is referred to as a first surgical instrument 212, and a second one of the two surgical instruments 212 and 214 that is controlled by manipulating the second handle unit 120R is referred to as a second surgical instrument 214.

Figure 7:
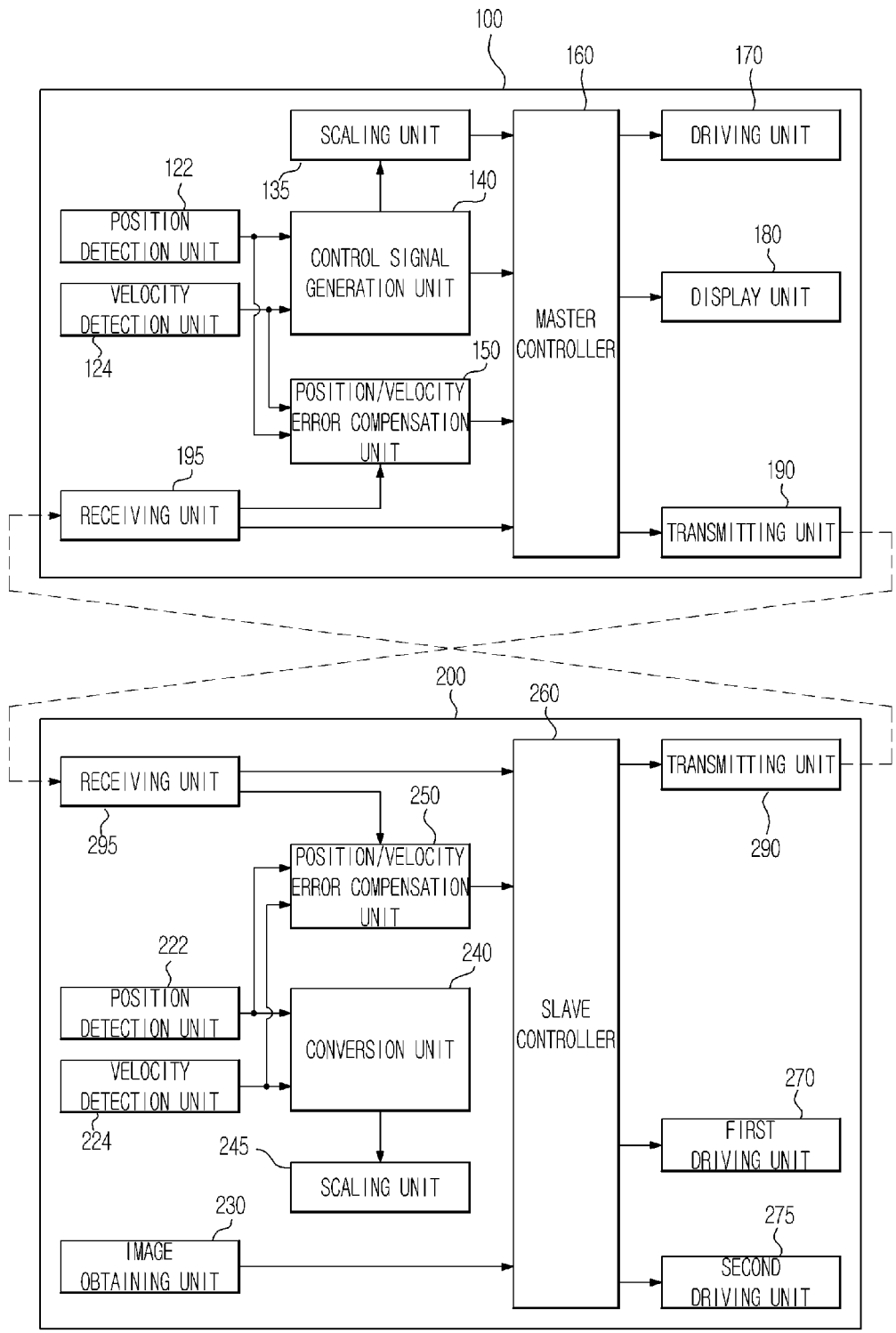
FIG. 7 is a block diagram illustrating a configuration of the surgical robot system according to an example embodiment

When the manipulator manipulates the first handle unit 120L and the second handle unit 120R with both hands, a master controller (see 160 of FIG. 7) of the master device 100 generates first operation control signals corresponding to state information of each of the first handle unit 120L and the second handle unit 120R manipulated using a control signal generation unit (see 140 of FIG. 7) and transmits the first operation control signals to the slave device 200 via a transmitting unit (see 190 of FIG. 7).

Here, the state information of the first handle unit 120L and the second handle unit 120R may include position, e.g., joint angle, information and velocity information regarding joints of each of the first handle unit 120L and the second handle unit 120R; however, example embodiments are not limited thereto. To this end, the master device 100 may include the position detection unit (see 122 of FIG. 7) and the velocity detection unit (see 124 of FIG. 7) for detecting position information and velocity information regarding joints of each of the first handle unit 120L and the second handle unit 120R.

Subsequently, a slave controller (see 260 of FIG. 7) of the slave device 200 may control an operation of the first surgical instrument 212 in response to one of the first operation control signals transmitted from the master device 100, for example, a control signal corresponding to the state information of the first handle unit 120L and may control an operation of the second surgical instrument 214 in response to a control signal corresponding to the state information of the second handle unit 120R.

The display unit 180 may be one or more monitors, as illustrated in FIG. 1. The display unit 180 may be implemented in such a way that pieces of information required for an operation may be individually displayed on each monitor. For example, when the display unit 180 includes three monitors, as illustrated in FIG. 1, real images collected by the endoscope 216 and virtual images obtained by converting medical images obtained before a patient's operation is performed into three-dimensional images may be displayed on one of three monitors. Further, information regarding an operating state of the slave device 200 and patient information may be displayed on the other two monitors. Alternatively, the same image may be displayed on a plurality of monitors. For example, the same image may be displayed on each monitor, or one image may be displayed on all of the plurality of monitors. Also, the number of monitors may be determined in various ways according to the type or kind of information to be displayed. The above-described display unit 180 may be a liquid crystal display (LCD) device, a light emitting diode (LED) display device, an organic light emitting diode (OLED) display device, a plasma display panel (PDP) display device, or a combination thereof; however, example embodiments are not limited thereto.

The "patient information" may be information indicating the state of the patient, for example, body information, such as temperature, pulse, respiration, and blood pressure. The slave device 200 that will be described below may include various units that are not illustrated, for example, a body information measurement unit including a temperature measurement module, a pulse measurement module, a respiration measurement module, and a blood pressure measurement module, so as to provide the body information to the master device 100. To this end, the master device 100 may further include a signal processor (not shown) that receives and processes the body information transmitted from the slave device 200 so as to output the body information to the display unit 180.

FIG. 2 illustrates the exterior of the slave device 200 of the surgical robot system illustrated in FIG. 1.

Referring to FIG. 2, the slave device 200 may include a caster unit 201, a body 202, robot arms 203 to 208, and a surgical instrument assembly 209.

The caster unit 201 may be used to move the slave device 200 and may be mounted on a lower end of the body 202. The caster unit 201 may include a plurality of casters, and a lever (not shown), disposed at each of the plurality of casters, that changes an operating state of the casters. The manipulator may change the operating state of the caster by adjusting a position of the lever (not shown). The operating state of the caster may include a freely swiveling state, a directionally locked state, and a swiveling locked state.

The robot arms 203 to 208 may be disposed at an upper part of the body 202. The robot arms 203 to 208 may move the surgical instrument assembly 209 along at least one of the x-axis, the y-axis, and the z-axis or may rotate the surgical instrument assembly 209 based on at least one axis. The robot arms 203 to 208 may support the surgical instrument assembly 209 so that the position and the orientation of the surgical instrument assembly 209 may be maintained while the operation is performed.

The robot arms 203 to 208 may include a plurality of link parts 204, 206, and 208, and a plurality of joint parts 203, 205, and 207. In detail, the robot arms 203 to 208 may include a first joint part 203, a first link part 204, a second joint part 205, a second link part 206, a third joint part 207, and a third link part 208.

The first link part 204 may include a first link and a casing that surrounds the first link. The first link may have a straight pillar shape and may be provided perpendicular to the body 202 such that the first link may be perpendicular to the ground.

The first joint part 203 may be disposed at a portion where the body 202 and the first link part 204 are connected to each other and may be implemented with a prismatic joint that moves along a designated axis among the x-axis, the y-axis, and the z-axis. The first joint part 203 is used to make a straight motion of the surgical instrument assembly 209 and may have three degrees of freedom (3 DOF). However, example embodiments are not limited thereto. A straight driving unit may be provided at the first joint part 203 provide the straight motion to the surgical instrument assembly 209. The straight driving unit may include a linear motion guide that guides a straight motion along a specific axis and a motor that provides a driving force to the linear motion guide.

The second link part 206 may be disposed on an end of the first link part 204 and may include a second link and a casing that surrounds the second link. The second link may have a curved shape, as illustrated in FIG. 2; however, example embodiments are not limited thereto.

The second joint part 205 may be disposed at a portion where the first link part 204 and the second link part 206 are connected to each other and may be implemented with a revolute joint that rotates based on a designated axis among the x-axis, the y-axis, and the z-axis. The second joint part 205 is used to make a rotational motion of the surgical instrument assembly 209 and may have two degrees of freedom (2 DOF); however, example embodiments are not limited thereto. The two degrees of freedom (2 DOF) may include rotation in a roll direction and rotation in a pitch direction; however, example embodiments are not limited thereto. A roll driving unit and a pitch driving unit may be provided at the second joint part 205 to provide the aforementioned rotation. The roll driving unit and the pitch driving unit may be implemented with a motor, a vacuum pump, and a hydraulic pump; however, example embodiments are not limited thereto.

The third link part 208 may be disposed on an end of the second link part 206 and may include a ring-shaped third link. The surgical instrument assembly 209 may be disposed at an upper part of the ring-shaped third link.

The third joint part 207 may be provided at a portion where the third link part 208 and the second link part 206 are connected to each other and may be implemented with a revolute joint that rotates based on a designated axis among the x-axis, the y-axis, and the z-axis. The third joint part 207 is used to make a rotational motion of the surgical instrument assembly 209 and may have one degree of freedom (1 DOF); however, example embodiments are not limited thereto. The one degree of freedom (1 DOF) may include rotation in a yaw direction; however, example embodiments are not limited thereto. To this end, a yaw driving unit may be provided at the third joint part 207. Here, the yaw driving unit may be implemented with a motor, a vacuum pump, and a hydraulic pump; however, example embodiments are not limited thereto.

The surgical instrument assembly 209 may include a cylindrical casing, the plurality of surgical instruments 212 and 214 provided along an inner circumferential surface of the casing, the endoscope 216, and the guide tube 210. Although the surgical instrument assembly 209 may further include a base station (not shown) to which the surgical instruments 212 and 214, the endoscope 216, and the guide tube 210 are fixed, example embodiments are not limited thereto. At least one surgical instrument selected by the manipulator from the plurality of surgical instruments 212 and 214 provided along the inner circumferential surface of the casing may enter the abdominal cavity of the patient via the guide tube 210.

The surgical instrument assembly 209 may be mechanically separated from the third link part 208. When the surgical instrument assembly 209 is separated from the third link part 208, the surgical instruments 212 and 214 may be relatively easily replaced with another one of the surgical instruments 212 and 214. Likewise, the surgical instruments 212 and 214 may be removed for sterilization in a relatively easy manner.

FIG. 3 illustrates the surgical instruments 212 and 214 unfolded through the guide tube 210.

As described previously, at least one surgical instrument 212 and 214 may enter the abdominal cavity of the patient along the guide tube 210. The surgical instruments 212 and 214 may enter the abdominal cavity of the patient via the guide tube 210 in various ways. In one example embodiment, the guide tube 210 is inserted into the abdominal cavity of the patient and is moved to a target position, e.g., the operating part, and then a motion of the guide tube 210 is fixed. Next, the surgical instruments 212 and 214 may be inserted into the abdominal cavity of the patient via a path provided at the guide tube 210 and then may be moved along the path and may enter the abdominal cavity of the patient. Before the guide tube 210 is inserted into the abdominal cavity of the patient, the endoscope 216 may be inserted into the guide tube 210. Therefore, as the guide tube 210 is inserted into the abdominal cavity of the patient, the endoscope 216 may be used to check an image inside the abdominal cavity and to move the guide tube 210 to the operating part.

In another example embodiment, the guide tube 210 enters the abdominal cavity of the patient in a state in which not only the endoscope 216 but also all of the surgical instruments 212 and 214 are inserted into the guide tube 210. Next, the guide tube 210 is moved to the operating part, the motion of the guide tube 210 is fixed, and the surgical instruments 212 and 214 are unfolded to an outside of the guide tube 210. FIG. 3 illustrates a shape in which two surgical instruments 212 and 214 and the endoscope 216 are unfolded to the outside of the guide tube 210.

Referring to FIG. 3, two surgical instruments 212 and 214 and the endoscope 216 may include a plurality of links 212b, 214b, and 216b, a plurality of joints 212c, 214c, and 216c, and end-effectors 212a, 214a, and 216a mounted on ends of the plurality of links 212b, 214b, and 216b. However, example embodiments are not limited thereto.

The above-described plurality of joints 212c, 214c, and 216c may be implemented with one among a fixed joint, a revolute joint that rotates along a designated axis among the x-axis, the y-axis, and the z-axis, and a prismatic joint that makes a straight motion along the designated axis among the x-axis, the y-axis, and the z-axis. Each of the joints 212c, 214c, and 216c may have one degree of freedom (1 DOF) or more.

A first driving unit (see 270 of FIG. 7) may be provided at each of the joints 212c, 214c, and 216c. The first driving unit 270 is driven in response to the first operation control signals received from the master device 100 and moves each joint. In this case, the first driving unit 270 may be implemented with one among a motor, a vacuum pump, and a hydraulic pump. However, example embodiments are not limited thereto. Hereinafter, the case where the first driving unit 270 is implemented with a motor will be described.

A detection unit may be provided at each of the joints 212c, 214c, and 216c. Here, the detection unit may include a position detection unit (see 222 of FIG. 7) that detects a position of each joint, e.g., a joint angle and a velocity detection unit (see 224 of FIG. 7) that detects the velocity of each joint.

The guide tube 210 may have a different degree of freedom (DOF) from that of the surgical instruments 212 and 214, and the degree of freedom (DOF) of the guide tube 210 may correspond to a redundant degree of freedom. Thus, the range of a working space for the surgical instruments 212 and 214 may be changed by controlling a motion of the guide tube 210.

Figure 5:
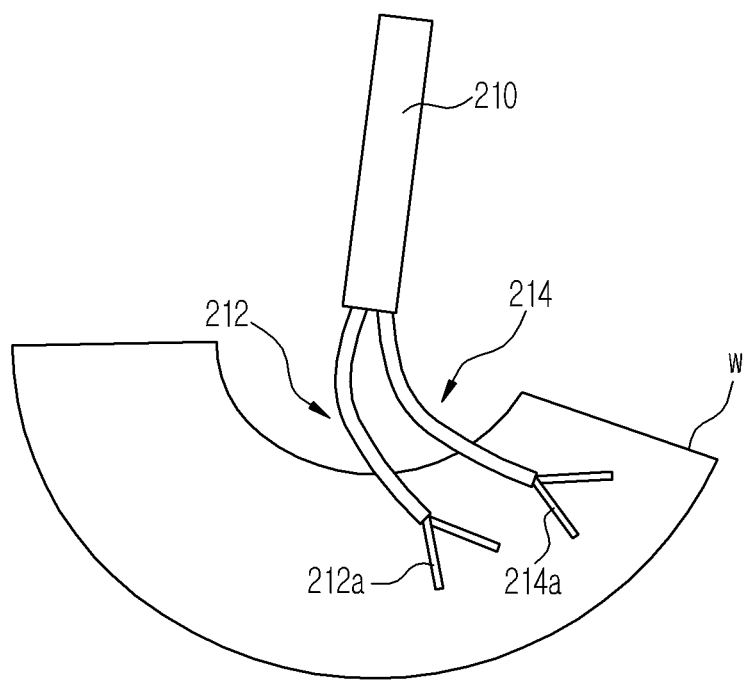
FIG. 5 illustrates a range of a working space for surgical instruments.
Figure 6:
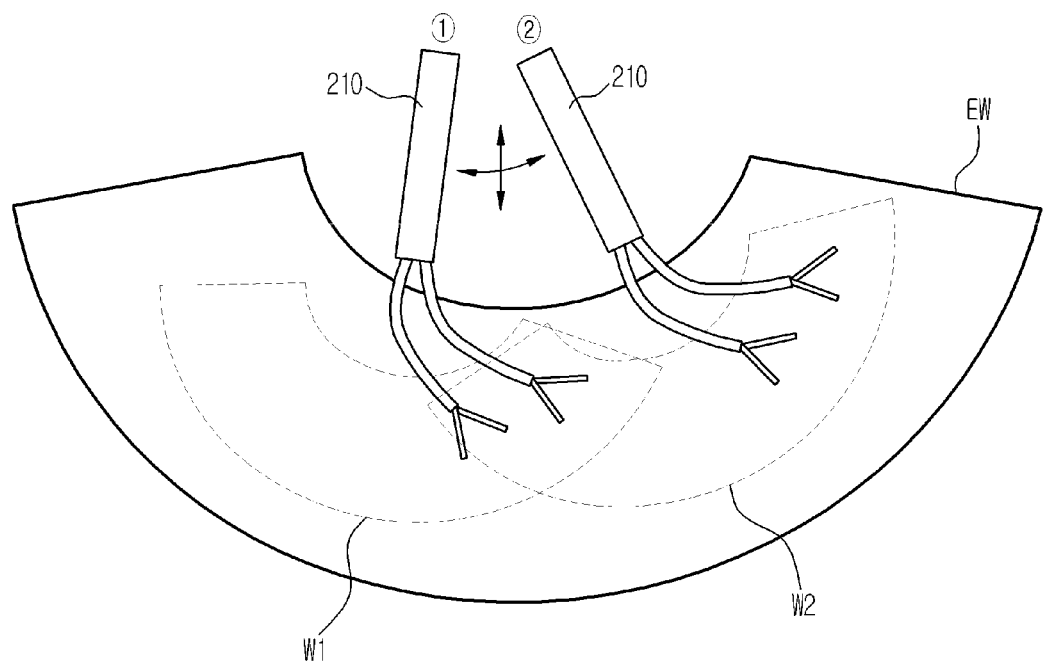
FIG. 6 illustrates an example in which the range of the working space for surgical instruments is extended according to a motion of the guide tube.

As illustrated in FIG. 5, a working space for the first surgical instrument 212 and the second surgical instrument 214 that is unfolded from the guide tube 210 in a state in which the guide tube 210 may be fixed as W. When the guide tube 210 operates, the working space W may change. For example, when the guide tube 210 changes to a state of $\hat{2}$ from a state of $\hat{1}$, as illustrated in FIG. 6, the working space W for the first surgical instrument 212 and the second surgical instrument 214 may be changed from $W_1$ to $W_2$.

In this way, as the guide tube 210 operates in the state of $\hat{2}$ from the state of $\hat{1}$, the working space W for the first surgical instrument 212 and the second surgical instrument 214 may be used from $W_1$ to $W_2$. As a result, the working space W for the first surgical instrument 212 and the second surgical instrument 214 may be extended to EW according to the motion of the guide tube 210.

Also, the guide tube 210 may operate due to a parallel motion or a rotational motion; however, example embodiments are not limited thereto.

The first handle unit 120L and the second handle unit 120R of the master device 100 generally have a degree of freedom (DOF) corresponding to that of the first surgical instrument 212 and the second surgical instrument 214. Thus, conventionally, a control signal used to control the operations of the first surgical instrument 212 and the second surgical instrument 214 and a control signal used to control a motion of the guide tube 214 may not be able to be simultaneously generated using the first handle unit 120L and the second handle unit 120R of the master device 100.

In order to solve this problem, the slave controller 260 of the slave device 200 not only controls the operations of the first surgical instrument 212 and the second surgical instrument 214 in response to the first operation control signals transmitted from the master device 100, but also controls the motion of the guide tube 210 according to circumstances. To this end, the first driving unit (see 270 of FIG. 7) that operates the first surgical instrument 212 and the second surgical instrument 214 and a second driving unit (see 275 of FIG. 7) that operates the guide tube 210 may be additionally provided at the slave device 200. This will be described below in detail.

In the surgical robot system, as illustrated in FIG. 5, the surgical instruments 212 and 214 may be unfolded from the end of the guide tube 210 in various directions, thus, ends of the surgical instruments 212 and 214, e.g., areas that the end-effectors 212a and 214a may contact, may be enlarged.

However, since the first surgical instrument 212 and the second surgical instrument 214 are connected to one guide tube 210, a distance between the end-effectors 212a and 214a of the first and second surgical instruments 212 and 214 is limited regardless of the motion of the guide 210. Thus, a target position of the first surgical instrument 212 and a target position of the second surgical instrument 214 cannot be simultaneously satisfied by moving the guide tube 210.

Figure 11:
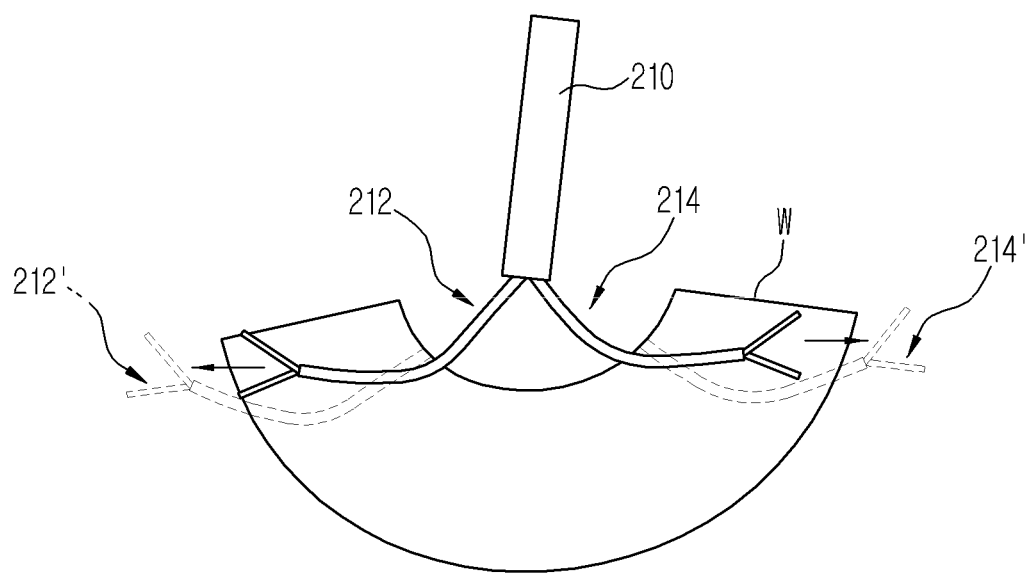
FIG. 11 illustrates a case where both of two surgical instruments are moved to the target position out of the current range of the working space.

For example, as illustrated in FIG. 11, when the manipulator manipulates the first handle unit 120L and the second handle unit 120R and instructs to simultaneously move the first surgical instrument 212 and the second surgical instrument 214 to target positions out of the range of the working space W, even when the guide tube 210 is moved, no common working space including the target position of the first surgical instrument 212 and the target position of the second surgical instrument 214 instructed by the manipulator may exist.

In this case, one of the first surgical instrument 212 and the second surgical instrument 214 to be firstly moved to the target position needs to be determined, and the guide tube 210 needs to be controlled to perform an operation of moving the determined surgical instrument to the target position.

When the guide tube 210 is moved, if both the first surgical instrument 212 and the second surgical instrument 214 cannot reach the target positions, the surgical robot system according to example embodiments feeds information regarding this state back to the master device 100 so that the manipulator may perceive this state.

Subsequently, the manipulator may determine a surgical instrument e.g. between the first surgical instrument 212 and the second surgical instrument 214 to be firstly moved to the target position, sustain a force applied to a handle unit corresponding to the determined surgical instrument and remove a force applied to a handle unit corresponding to the other surgical instrument that is not to be moved. The master controller 160 of the master device 100 may detect state information of the handle unit from which the force is removed, generates a control signal corresponding to the detected state information, and transmit the generated control signal to the slave device 200. This will be described below in greater detail.

Next, the configuration of the surgical robot system illustrated in FIG. 7 will be described in detail.

FIG. 7 is a block diagram illustrating a configuration of the surgical robot system according to an example embodiment.

Master Device

Referring to FIG. 7, the master device 100 of the surgical robot system may include a position detection unit 122, a velocity detection unit 124, a scaling unit 135, a control signal generation unit 140, a position/velocity error compensation unit 150, a master controller 160, a driving unit 170, a display unit 180, a transmitting unit 190, and a receiving unit 195.

The position detection unit 122 may be provided at each joint of the first handle unit 120L and the second handle unit 120R and detect the position of each joint, e.g., a joint angle. The position detection unit 122 may be a position sensor, for example, a potentiometer or an encoder. However, example embodiments are not limited thereto. The position of each joint of the first handle unit 120L and the second handle unit 120R detected by the position detection unit 122 may be provided to the control signal generation unit 140 and the position/velocity error compensation unit 150, respectively.

The velocity detection unit 124 is provided at each joint of the first handle unit 120L and the second handle unit 120R and detects the velocity of each joint. The velocity detection unit 124 may be a velocity sensor, for example. The velocity of each joint of the first handle unit 120L and the second handle unit 120R detected by the velocity detection unit 124 may be provided to the control signal generation unit 140 and the position/velocity error compensation unit 150, respectively.

In FIG. 7, the master device 100 includes both the position detection unit 122 and the velocity detection unit 124. However, the velocity detection unit 124 may be omitted according to circumstances and a velocity signal may be obtained by a velocity calculation unit (not shown) that calculates the velocity signal by differentiating the position signal detected by the position detection unit 122.

The control signal generation unit 140 is configured to generate a target position and a target velocity to be followed by each joint of the surgical instruments 212 and 214 of the slave device 200 using the position and velocity of each joint of the first handle unit 120L and the second handle unit 120R detected by the position detection unit 122 and the velocity detection unit 124 described above.

Hereinafter, for convenience of explanation, the target position and the target velocity generated by the control signal generation unit 140 of the master device 100 will be referred to as being part of the first operation control signals. That is, the first operation control signals may be understood as signals regarding motions of the handle units 120L and 120R to be followed by the surgical instruments 212 and 214. The first operation control signals generated by the control signal generation unit 140 may be provided to the scaling unit 135.

The scaling unit 135 is configured to scale the first operation control signals output by the control signal generation unit 140 at a desired (or alternatively, a predetermined) reduction ratio. In this case, the scaling unit 135 may apply a motion scaling factor to each of the target position and the target velocity of the first operation control signals. Here, the motion scaling factor may be defined as '1/n' (where n is a natural number) and may not be changed or may be changed by the manipulator.

Also, the motion scaling factor applied to the target position and the motion scaling factor applied to the target velocity may be the same value or different values. In this way, when these motion scaling factors are applied to the first operation control signals generated by the control signal generation unit 140, a ratio of motions of the first surgical instrument 212 and the second surgical instrument 214 with respect to motions of the first handle unit 120L and the second handle unit 120R may be adjusted.

As described above, the scaled first operation control signals output from the scaling unit 135 may be provided to the master controller 160.

The receiving unit 195 may operate by pairing with a transmitting unit 290 of the slave device 200. The receiving unit 195 may receive image data and the target position and the target velocity to be followed by each joint of the handle units 120L and 120R from the slave device 200. In this case, the target position and the target velocity to be followed by each joint of the handle units 120L and 120R may be scaled at an enlargement ratio output from a scaling unit 245 of the slave device 200.

The position/velocity error compensation unit 150 is configured to compare the target position and the target velocity to be followed by each joint of the handle units 120L and 120R received by the receiving unit 195 from the slave device 200 with a current position and a current velocity of each joint of the handle units 120L and 120R detected by the position detection unit 122 and the velocity detection unit 124 of the master device 100. The position/velocity error compensation unit 150 is further configured to generate a control signal for compensating for a difference between the target position/velocity and the current position/velocity.

Hereinafter, for convenience of explanation, a control signal generated by the position/velocity error compensation unit 150 of the master device 100 will be referred to as a first compensation control signal. The first compensation control signal may be a signal used to control the motions of the handle units 120L and 120R so as to follow the motions of the surgical instruments 212 and 214. The first compensation control signal generated by the position/velocity error compensation unit 150 may be provided to the master controller 160.

The master controller 160 provides a control signal to the driving unit 170 provided at each joint of the handle units 120L and 120R. In detail, the master controller 160 may provide the first compensation control signal to the driving unit 170. Thus, a force to follow the motions, e.g., the position and velocity of the first surgical instrument 212 and the second surgical instrument 214 may be generated in each of the first handle unit 120L and the second handle unit 120R of the master device 100. In this way, the manipulator may intuitively determine whether each of the first surgical instrument 212 and the second surgical instrument 214 is close to a boundary surface of the working space W, based on the force generated in each of the first handle unit 120L and the second handle unit 120R. Hereinafter, for convenience of explanation, the force generated in each of the first handle unit 120L and the second handle unit 120R will be referred to as a feedback force.

Figure 12:
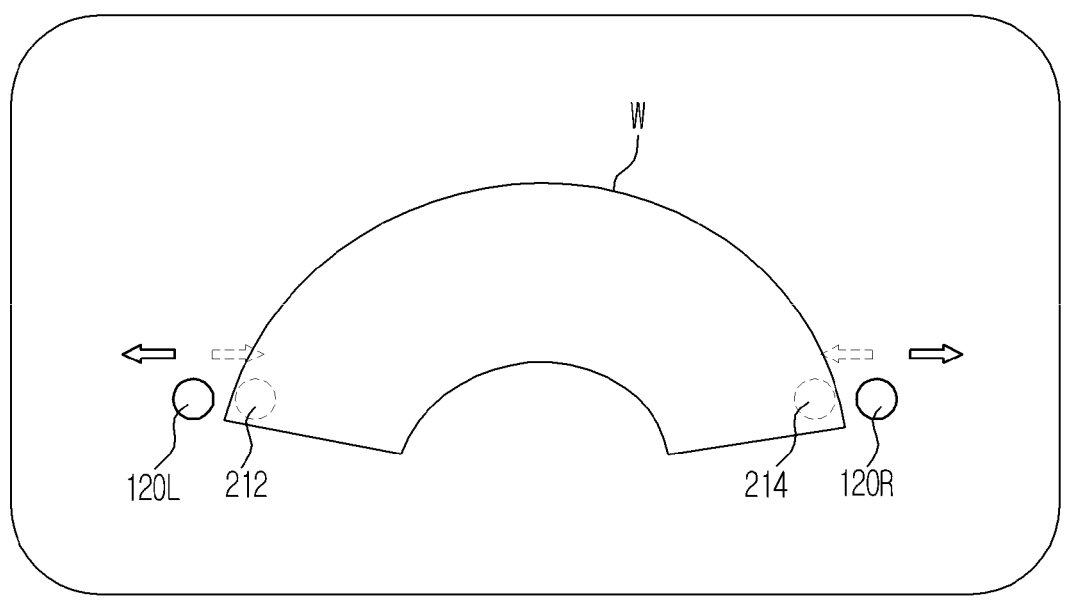
FIG. 12 illustrates the relationship between a manipulator's force applied to the handle units of the master device and a feedback force generated in the handle units of the master device.

For example, as illustrated in FIG. 12, when the first surgical instrument 212 and the second surgical instrument 214 are placed at the boundary surface of the working space W and cannot be spread further apart, if the same force is applied by the manipulator to the first handle unit 120L and the second handle unit 120R in a solid arrow direction, the first surgical instrument 212 and the second surgical instrument 214 may not be moved any more, and simultaneously, a feedback force corresponding to this state may be generated in each of the first handle unit 120L and the second handle unit 120R held by the manipulator so that the manipulator may know this state.

In this case, the feedback force generated in each of the first handle unit 120L and the second handle unit 120R may be generated by operating the first handle unit 120L and the second handle unit 120R to follow the position and velocity of each of the first surgical instrument 212 and the second surgical instrument 214 in response to the first compensation control signal generated by the position/velocity error compensation unit 150. The feedback force may be calculated using Equation 1 below:

$$f_{mst,i} = k_{mst}(x_{slv,i} - x_{mst,i}) + b_{mst}(v_{slv,i} - v_{mst,i}) \quad \text{(Equation 1)}$$

In equation 1, $f_{mst}$ is a force generated in each handle unit, $x_{slv}$ is a current position of a surgical instrument, $x_{mst}$ is a target position of the surgical instrument, $v_{slv}$ is a current velocity of the surgical instrument, $v_{mst}$ is a target velocity of the surgical instrument, $k_{mst}$ is a control gain with respect to a position, $b_{mst}$ is a control gain with respect to velocity, and i is an index of the surgical instrument.

That is, a direction of the force applied by the manipulator and a direction of the feedback force generated in the handle units 120L and 120R in response to the first compensation control signal are opposite to each other. Thus, the manipulator may perceive the feedback force generated in an opposite direction to the direction of the force applied by the manipulator and may determine whether the first surgical instrument 212 and the second surgical instrument 214 are close to the boundary surface of the working space W.

The master controller 160 transmits data to the slave device 200 via the transmitting unit 190. In detail, the master controller 160 may transmit the first operation control signal scaled by the scaling unit 135 to the slave device 200.

The master controller 160 may perform image processing on the image data received by the receiving unit 195. Examples of image processing may include enlarging, reducing, moving, rotating, editing, and filtering of a captured image; however, example embodiments are not limited thereto. However, this image processing does not need to be performed by the master controller 160.

The display unit 180 may display image data, for example, image data processed by the master controller 160.

The driving unit 170 may be provided at each joint of the first handle unit 120L and the second handle unit 120R. The driving unit 170 may be driven in response to the first compensation control signal provided from the master controller 160 and may move or rotate each joint of the first handle unit 120L and the second handle unit 120R. Thus, the first handle unit 120L and the second handle unit 120R may be driven with an operation of following motions of the first surgical instrument 212 and the second surgical instrument 214.

The transmitting unit 190 may be configured to operate by pairing with a receiving unit 295 of the slave device 200. The transmitting unit 190 may transmit signals provided from the master controller 160, e.g., the first operation control signals scaled by the scaling unit 135 to the receiving unit 295 of the slave device 200.

Slave Device

Referring to FIG. 7, the slave device 200 may include a position detection unit 222, a velocity detection unit 224, an image obtaining unit 230, a conversion unit 240, the scaling unit 245, a position/velocity error compensation unit 250, a slave controller 260, a first driving unit 270, a second driving unit 275, the transmitting unit 290, and the receiving unit 295.

The position detection unit 222 may be provided at each joint of the first surgical instrument 212 and the second surgical instrument 214 and may detect the position of each joint, e.g., a joint angle. The position detection unit 222 may be implemented with a position sensor, for example, a potentiometer or an encoder; however, example embodiments are not limited thereto. The position of each joint of the first surgical instrument 212 and the second surgical instrument 214 detected by the position detection unit 222 may be provided to the conversion unit 240 and the position/velocity error compensation unit 250, respectively.

The velocity detection unit 224 may be provided at each joint of the first surgical instrument 212 and the second surgical instrument 214 and may detect the velocity of each joint. The velocity detection unit 224 may be implemented with a velocity sensor, for example. The velocity of each joint of the first surgical instrument 212 and the second surgical instrument 214 detected by the velocity detection unit 224 may be provided to the conversion unit 240 and the position/velocity error compensation unit 250, respectively.

In FIG. 7, the slave device 200 includes both the position detection unit 222 and the velocity detection unit 224. However, the velocity detection unit 224 may be omitted according to circumstances and a velocity calculation unit (not shown) may be provided that calculates a velocity signal by differentiating the position signal detected by the position detection unit 222.

The conversion unit 240 is configured to convert the position and velocity of each joint of the first surgical instrument 212 and the second surgical instrument 214, detected by the position detection unit 222 and the velocity detection unit 224, into a target position and a target velocity to be followed by each joint of the first handle unit 120L and the second handle unit 120R of the master device 100.

Hereinafter, for convenience of explanation, the target position and the target velocity generated by the conversion unit 240 of the slave device 200 will be referred to as being part of second operation control signals. That is, the second operation control signals may be understood as signals regarding motions of the first surgical instrument 212 and the second surgical instrument 214 to be followed by the first handle unit 120L and the second handle unit 120R. The second operation control signals generated by the conversion unit 240 may be provided to the scaling unit 245.

The scaling unit 245 may scale the second operation control signals output by the conversion unit 240 at a desired (or alternatively, a predetermined) enlargement ratio. To this end, the scaling unit 245 may apply a motion scaling factor to each of the target position and the target velocity of the second operation control signals output from the conversion unit 240. Here, the motion scaling factor to be applied by the scaling unit 245 of the slave device 200 may be defined as an inverse number n of the motion scaling factor used in the scaling unit 135 of the master device 100. In this way, the second operation control signals scaled by the scaling unit 245 at an enlargement ratio may be provided to the slave controller 260.

The receiving unit 295 may operate by pairing with the transmitting unit 190 of the master device 100. The receiving unit 295 may receive data from the master device 100. In detail, the receiving unit 295 may receive first operation control signals scaled by the master device 100 at a reduction ratio. The first operation control signals scaled at the reduction ratio among the received data may be provided to the position/velocity error compensation unit 250.

The position/velocity error compensation unit 250 may be configured to compare the target position and the target velocity to be followed by each joint of the first surgical instrument 212 and the second surgical instrument 214 included in the first operation control signals scaled at the reduction ratio with a current position and a current velocity of each joint of the first surgical instrument 212 and the second surgical instrument 214 detected by the position detection unit 222 and the velocity detection unit 224 of the slave robot 200. The position/velocity error compensation unit 250 may further be configured to generate a control signal for compensating for a difference between the target position/velocity and the current position/velocity.

Hereinafter, for convenience of explanation, a control signal generated by the position/velocity error compensation unit 250 of the slave device 200 will be referred to as a second compensation control signal. The second compensation control signal may be a motion control signal used to control the motions of the first surgical instrument 212 and the second surgical instrument 214 so as to follow the motions of the first handle unit 120L and the second handle unit 120R. The second compensation control signal generated by the position/velocity error compensation unit 250 may be provided to the slave controller 260.

The image obtaining unit 230 may obtain image data. For example, the image obtaining unit 230 may obtain image data regarding the operating part by photographing an inside of the abdominal cavity of the patient. The image obtaining unit 230 may be the endoscope 216 described with reference to FIG. 3; however, example embodiments are not limited thereto. The image data obtained by the image obtaining unit 230 may be provided to the slave controller 260.

The slave controller 260 may provide a control signal to the first driving unit 270 provided at each joint of the first surgical instrument 212 and the second surgical instrument 214. In detail, the slave controller 260 may provide the second compensation control signal provided by the position/velocity error compensation unit 250 to the first driving unit 270.

Also, the slave controller 260 may provide data to be transmitted to the master device 100 to the transmitting unit 290. The data may be the second operation control signals scaled by the scaling unit 245 at the enlargement ratio; however, example embodiments are not limited thereto.

Also, the slave controller 260 may perform image processing on the image data obtained by the image obtaining unit 230. Examples of image processing may include enlarging, reducing, moving, rotating, editing, and filtering of a captured image; however, example embodiments are not limited thereto. However, this image processing does not need to be performed by the slave controller 260.

The first driving unit 270 may be configured to be provided at each joint of the first surgical instrument 212 and the second surgical instrument 214. The first driving unit 270 may transmit a driving force to each joint of the first surgical instrument 212 and the second surgical instrument 214. In detail, the first driving unit 270 may be driven in response to the second compensation control signal provided from the position/velocity error compensation unit 250 and move or rotate each joint of the first surgical instrument 212 and the second surgical instrument 214.

Thus, the first surgical instrument 212 and the second surgical instrument 214 may be driven with an operation of following motions the first handle unit 120L and the second handle unit 120R. In this case, the number of first driving units 270 corresponding to the number of the surgical instruments 212 and 214 may be provided; however, example embodiments are not limited thereto. For example, since two surgical instruments including the first surgical instrument 212 and the second surgical instrument 214 are provided, two first driving units 270 may be provided.

The second driving unit 275 is configured to be provided at the guide tube 210 and to transmit a driving force to the guide tube 210. In detail, the second driving unit 275 may provide the driving force to the guide tube 210 in such a way that the guide tube 210 may perform an operation including a rotational motion and a parallel motion in response to the second compensation control signal through control performed by the slave controller 260.

In addition, the slave controller 260 may provide control signals both to the first driving unit 270 and the second driving unit 275 or may provide a control signal only to one of the first driving unit 270 and the second driving unit 275. This will be described below in detail.

The slave controller 260 provides the second compensation control signal provided from the position/velocity error compensation unit 250 to the first driving unit 270, and the first driving unit 270 transmits the driving force to each joint of the first surgical instrument 212 and the second surgical instrument 214 in response to the second compensation control signal in such a way that the first surgical instrument 212 and the second surgical instrument 214 may operate to follow motions of the first handle unit 120L and the second handle unit 120R. In this case, a force (torque) generated in the first surgical instrument 212 and the second surgical instrument 214 may be calculated using Equations 2 to 4, described below.

$$f_{slv,i}{}^0 = k_{slv}(x_{mst,i} - x_{slv,i}) + b_{slv}(v_{mst,i} - v_{slv,i}) \quad \text{(Equation 2)}$$

Equation 2 corresponds to Equation 1 above but from the point of view of the slave device 200. The force (torque) to be generated in the surgical instruments 212 and 214 is obtained using Equation 2. In this case, when the first surgical instrument 212 or the second surgical instrument 214 is placed at a boundary surface $\partial W$ of the working space W, the force (torque) may be decomposed into a vertical vector component and a tangential vector component with respect to the boundary surface $\partial W$ and may be shown in Equation 3 below:

$$f_{slv,i}{}^0 = f_{slv,i}{}^0|_{\partial W} + f_{slv,i}{}^0|_{\partial W^\perp} \quad \text{(Equation 3)}$$

In Equation 3, the former term $f_{slv,i}{}^0|_{\partial W}$ is the tangential vector component with respect to the boundary surface $\partial W$, and the latter term $f_{slv,i}{}^0|_{\partial W^\perp}$ is the vertical vector component with respect to the boundary surface $\partial W$.

The tangential vector component with respect to the boundary surface may be calculated by projection with respect to the boundary surface. Finally, the force (torque) to be generated in the first surgical instrument 212 and the second surgical instrument 214 may be calculated using Equation 4 below, obtained by modifying Equation 2 above:

$$f_{slv,i} = \begin{cases} f_{slv,i}^0|_{\partial W} & \text{if } x_{slv,i} \in \partial W \text{ and } f_{slv,i}^0|_{\partial W^\perp} \text{ is outward} \\ f_{slv,i}^0 & \text{otherwise} \end{cases} \quad \text{(Equation 4)}$$

That is, in Equation 4, the force to be generated in the surgical instruments 212 and 214 is obtained in each of the case where the surgical instruments 212 and 214 are placed at the boundary surface $\partial W$ of the working space W and the force to be applied to the surgical instruments 212 and 214 is outwards from the boundary surface $\partial W$ of the working space W ($x_{slv,i} \in \partial W$ and $f_{slv,i}{}^0|_{\partial W^\perp}$ is outward) and the other case otherwise.

In detail, as a result of calculating the force to follow motions of the handle units 120L and 120R (Equation 2), when the surgical instruments 212 and 214 are placed inside the working space W for the surgical instruments 212 and 214, the force to be generated in the surgical instruments 212 and 214 may be calculated using a value obtained by multiplying a value obtained by subtracting current positions from target positions of the surgical instruments 212 and 214 by a position control gain $k_{slv}$ and using a value obtained by multiplying a value obtained by subtracting current velocity from target velocity of the surgical instruments 212 and 214 by a velocity control gain $b_{slv}$.

Also, even when the surgical instruments 212 and 214 are placed at the boundry surface of the working space W for the surgical instruments 212 and 214, if the force to be generated in the surgical instruments 212 and 214 is not outwards from the boundary space of the working space W, the force to be generated in the surgical instruments 212 and 214 may be calculated in the same manner.

Meanwhile, when the surgical instruments are placed at the boundary surface of the working space W and a direction of the force calculated using Equation 2 is outwards from the working space W for the surgical instruments 212 and 214, the force to be generated in the surgical instruments 212 and 214 may be calculated using a value obtained by projecting the value obtained by multiplying a value obtained by subtracting current positions from target positions of the surgical instruments 212 and 214 by the position control gain $k_{slv}$ and the value obtained by multiplying a value obtained by subtracting current velocity from target velocity of the surgical instruments 212 and 214 by the velocity control gain $b_{slv}$ onto the boundary surface $\partial W$.

Also, the slave controller 260 may determine whether the first surgical instrument 212 and the second surgical instrument 214, that are operating, are close to the boundary surface of the working space W and whether the target positions included in the first operation control signal are out of the range of the working space W for the first surgical instrument 212 and the second surgical instrument 214.

If it is determined that the first surgical instrument 212 and the second surgical instrument 214 that are operating are close to the boundary surface of the working space W and the target position of the first surgical instrument 212 or the target position of the second surgical instrument 214 included in the first operation control signal is out of the range of the current working space W, the slave controller 260 may provide the second compensation control signal to the second driving unit 275 and may operate the guide tube 210 to make a parallel or rotational motion so that the first surgical instrument 212 or the second surgical instrument 214 may reach the target position. In this case, a force (torque) generated when the guide tube 210 makes a parallel motion and a force (torque) generated when the guide tube 210 makes a rotation motion may be calculated using Equation 5 and Equation 6 below:

$$f_{GT} = \sum_i f_{GT,i} \quad \text{(Equation 5)}$$

$$M_{GT} = \sum_i r_{GT,i} \times f_{GT,i} \quad \text{(Equation 6)}$$

Here, $f_{GT,i}$ may be calculated using Equation 7 below, and $r_{GT,i}$ may be calculated using Equation 8 below:

$$f_{GT,i} = \begin{cases} a_{GT} f_{slv,i}^0|_{\partial W^\perp} & \text{if } x_{slv,i} \in \partial W \text{ and } f_{slv,i}^0|_{\partial W^\perp} \text{ is outward} \\ 0 & \text{otherwise} \end{cases} \quad \text{(Equation 7)}$$

Here, $a_{GT}$ is a relative gain with respect to a force to be generated in the guide tube 210.

In Equation 7, the force to be generated in the guide tube 210 is obtained in each of the case where the surgical instruments 212 and 214 are currently placed at the boundary surface $\partial W$ of the working space W and a force $f_{slv,i}{}^0$ to be applied to the surgical instruments 212 and 214 is outwards from the boundary surface $\partial W$ of the working space W ($x_{slv,i} \in \partial W$ and $f_{slv,i}{}^0|_{\partial W^\perp}$ outward) and the case where the surgical instruments 212 and 214 are placed within the working space W or at the boundary surface $\partial W$ of the working space W and the force $f_{slv,i}{}^0$ to be applied to the surgical instruments 212 and 214 is inwards from the boundary surface ∂W of the working space W(otherwise).

That is, as a result of calculating the force to follow the motions of the handle units 120L and 120R, in detail, when the surgical instruments 212 and 214 are currently placed at the boundary surface ∂W of the working space W for the surgical instruments 212 and 214 and the force $f_{slv,i}^0$ to be applied to the surgical instruments 212 and 214 is outwards from the boundary surface ∂W of the working space W, the force to be applied in the guide tube 210 may be calculated using a value obtained by vertically projecting the value obtained by multiplying a value obtained by subtracting current positions from target positions of the surgical instruments 212 and 214 by the position control gain $k_{slv}$ and the value obtained by multiplying a value obtained by subtracting current velocity from target velocity of the surgical instruments 212 and 214 by the velocity control gain $b_{slv}$ onto the boundary surface ∂W.

Meanwhile, when the surgical instruments 212 and 214 are placed within the working space W or at the boundary surface ∂W and the force $f_{slv,i}^0$ to be applied to the surgical instruments 212 and 214 is not outwards from the working space W, the force to be generated in the guide tube 210 is 0.

$$r_{GT,i} = x_{slv,i} - c \quad \text{(Equation 8)}$$

In Equation 8, c is a rotation center of the working space W.

One Surgical Instrument Out of Range

In a first case, only the target position of one, e.g., of the first surgical instrument 212 and the second surgical instrument 214 may be out of the range of the working space W. In a second case, both the target positions of the first surgical instrument 212 and the target position of the second surgical instrument 214 may be out of the range of the working space W.

Figure 10:
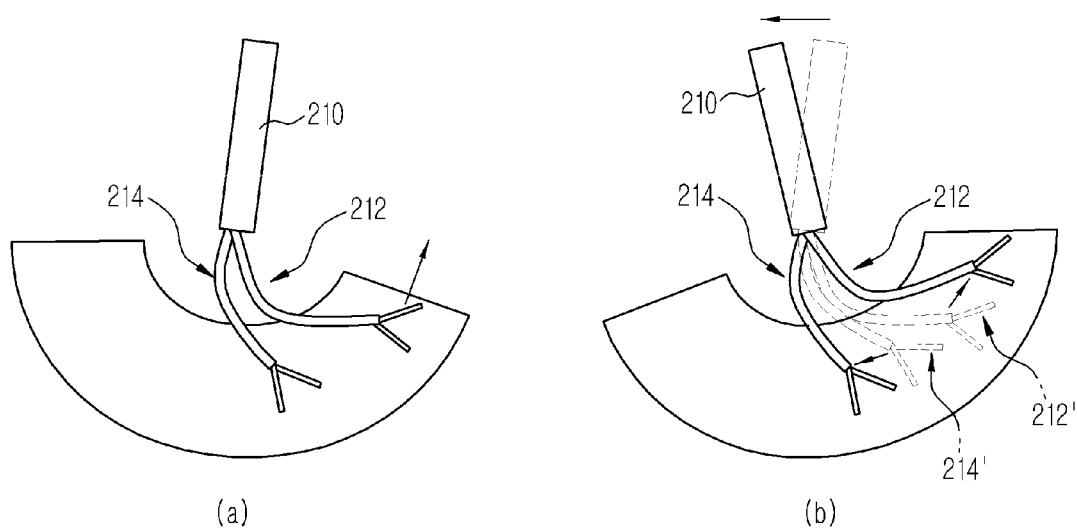
FIG. 10 illustrates an example in which one of two surgical instruments is moved to a target position due to the motion of the guide tube and the other one thereof is moved to its original position.

In e.g. the first case where only the target position of one surgical instrument, e.g., the first surgical instrument 212 is out of the range of the working space W in an arrow direction, as illustrated in FIG. 10A, the slave controller 260 may operate as follows.

The slave controller 260 may control the slave device 200 to provide the second compensation control signal to the second driving unit 275 and to move the guide tube 210 in the arrow direction, as illustrated in FIG. 10B. Further, slave controller 260 may not provide the second compensation control signal to the first driving unit 270 corresponding to the first surgical instrument 212 in such a way that the first surgical instrument 212 may reach the target position due to only a motion of the guide tube 210 in a state in which the first surgical instrument 212 stops.

When the guide tube 210 is moved in the arrow direction, as illustrated in FIG. 10B, the first surgical instrument 212 is moved from its original position 212' to the arrow direction and reaches the target position, and simultaneously, the second surgical instrument 214 is moved to a target position 214'. Since the second surgical instrument 214 needs to be maintained at not the target position 214' but a position corresponding to the motion of the second handle unit 120R, the slave controller 260 may control the slave device 200 to provide a control signal generated by manipulating the second handle unit 120R to the first driving unit 270 corresponding to the second surgical instrument 214 in such a way that the second surgical instrument 214 may be moved from the target position 214' to a direction in which the motion of the guide tube 210 is offset, e.g., to the arrow direction and the second surgical instrument 214 may follow the motion of the second handle unit 120R.

Both Surgical Instruments Out of Range of the Current Working Space

In the second case e.g. where the target position 212' of the first surgical instrument 212 and the target position 214' of the second surgical instrument 214 are out of the range of the working space W, as illustrated in FIG. 11, the slave controller 260 may operate as follows.

A Working Space Exists that Includes Target Positions of Both Surgical Instruments The slave controller 260 may provide the second compensation control signal to the second driving unit 275 so as to operate the guide tube 210, wherein the current working space W of the first surgical instrument 212 and the second surgical instrument 214 may be changed into the working space W including both the target position of the first surgical instrument 212 and the target position of the second surgical instrument 214. Further, the slave controller 260 may not provide the second compensation control signal to the first driving unit 270 corresponding to each of the first surgical instrument 212 and the second surgical instrument 214 in such a way that the first surgical instrument 212 and the second surgical instrument 214 may be maintained in a stop state.

A Working Space does not Exist that Includes Target Positions of Both Surgical Instruments However, when there is no working space in which both the target position of the first surgical instrument 212 and the target position of the second surgical instrument 214 may be included, the slave controller 260 may operate the guide tube 210 in such a way that a vector sum of the current position and the target position of each of the first surgical instrument 212 and the second surgical instrument 214 may be minimized. That is, the slave controller 260 may operate the guide tube 210 so that the current working space W of the first surgical instrument 212 and the second surgical instrument 214 may be changed into the working space W including both a position that is closest to the target position of the first surgical instrument 212 and a position that is closest to the target position of the second surgical instrument 214.

The slave controller 260 may perform the following operation so as to inform the manipulator of no working space including both the target position of the first surgical instrument 212 and the target position of the second surgical instrument 214, as described above.

For example, the slave controller 260 detects state information about the first surgical instrument 212 and the second surgical instrument 214, for example, a current position and a current velocity of the first surgical instrument 212 and the second surgical instrument 214, and provides the detected current position and current velocity to the master device 100. The state information may be detected by the position detection unit 222 and the velocity detection unit 224, as described above. The current position and current velocity of the first surgical instrument 212 and the second surgical instrument 214 detected in this way are converted by the conversion unit 240 into second operation control signals. The second operation control signals being signals regarding motions of the first surgical instrument 212 and the second surgical instrument 214 that are to be followed by the first handle unit 120L and the second handle unit 120R. The second operation control signals may be scaled by the scaling unit 245 at a desired (or alternatively, a predetermined) enlargement ratio and then transmitted by the transmitting unit 290 to the master device 100.

The master device 100 may generate a first compensation control signal for comparing the second operation control signals with the current position and the current velocity of each of the handle units 120L and 120R detected by the position detection unit 122 and the velocity detection unit 124 and for compensating for a difference therebetween using the position/velocity error compensation unit 150. The master controller 160 may provide the first compensation control signal to the driving unit 170. The driving unit 170 may transmit a driving force generated by the first compensation control signal to each joint of the first handle unit 120L and the second handle unit 120R so that the first handle unit 120L and the second handle unit 120R may operate to follow the motions of the first surgical instrument 212 and the second surgical instrument 214.

Thus, a feedback force to follow the position and velocity of each of the first surgical instrument 212 and the second surgical instrument 214 may be generated in each of the first handle unit 120L and the second handle unit 120R, and the manipulator perceives the feedback force generated in this way, thereby intuitively determining whether each of the first surgical instrument 212 and the second surgical instrument 214 is close to the boundary surface of the working space W.

When target positions of all of the surgical instruments 212 and 214 are out of the range of the working space W, a priority to move a target position that is an example of a priority regarding the first surgical instrument 212 and the second surgical instrument 214 that are close to the boundary surface of the working space W through manipulator's manipulation may be determined. The first handle unit 120L or the second handle unit 120R may need to be manipulated by the manipulator in a direction in which the feedback force is offset.

In this regard, referring to FIG. 12, when both the first surgical instrument 212 and the second surgical instrument 214 are placed at the boundary surface of the working space W, if the manipulator applies the same force to the first handle unit 120L and the second handle unit 120R in an arrow direction (indicated by the solid line) so as to simultaneously move the first surgical instrument 212 and the second surgical instrument 214 to their target positions that are out of the range of the working space W, the first surgical instrument 212 and the second surgical instrument 214 are in a stop state in which they do not operate, and the feedback force corresponding to this state may be generated in the first handle unit 120L and the second handle unit 120R in an arrow direction (indicated by the dotted line) so that the manipulator may perceive this state.

Subsequently, the manipulator who perceives the feedback force generated in the first handle unit 120L and the second handle unit 120R determines which one of the first surgical instrument 212 and the second surgical instrument 214 to be firstly moved to the target position. The manipulator may maintain the force applied to the handle unit corresponding to the surgical instrument to be firstly moved to the target position, and manipulate the handle unit corresponding to the other surgical instrument in a direction in which the feedback force is offset.

In this regard, referring to FIG. 12, if the manipulator determines to firstly move the first surgical instrument 212 to the target position in the above-described state, the manipulator maintains the force (arrow direction indicated by the solid line) applied to the first handle unit 120L for controlling the first surgical instrument 212 and removes the force (arrow direction indicated by the solid line) applied to the second handle unit 120R for controlling the second surgical instrument 214. That is, the manipulator manipulates the second handle unit 120R in a direction in which the feedback (arrow direction indicated by the dotted line) generated in the second handle unit 120R is offset.

Thus, the second surgical instrument 214 may be moved in the same direction as the direction of the target position of the first surgical instrument 212. As a result, the range of the working space W is changed, and the first surgical instrument 212 may be moved to the target position required by the manipulator, and both the first surgical instrument 212 and the second surgical instrument 214 may be included in the range of the changed working space W.

Figure 13:
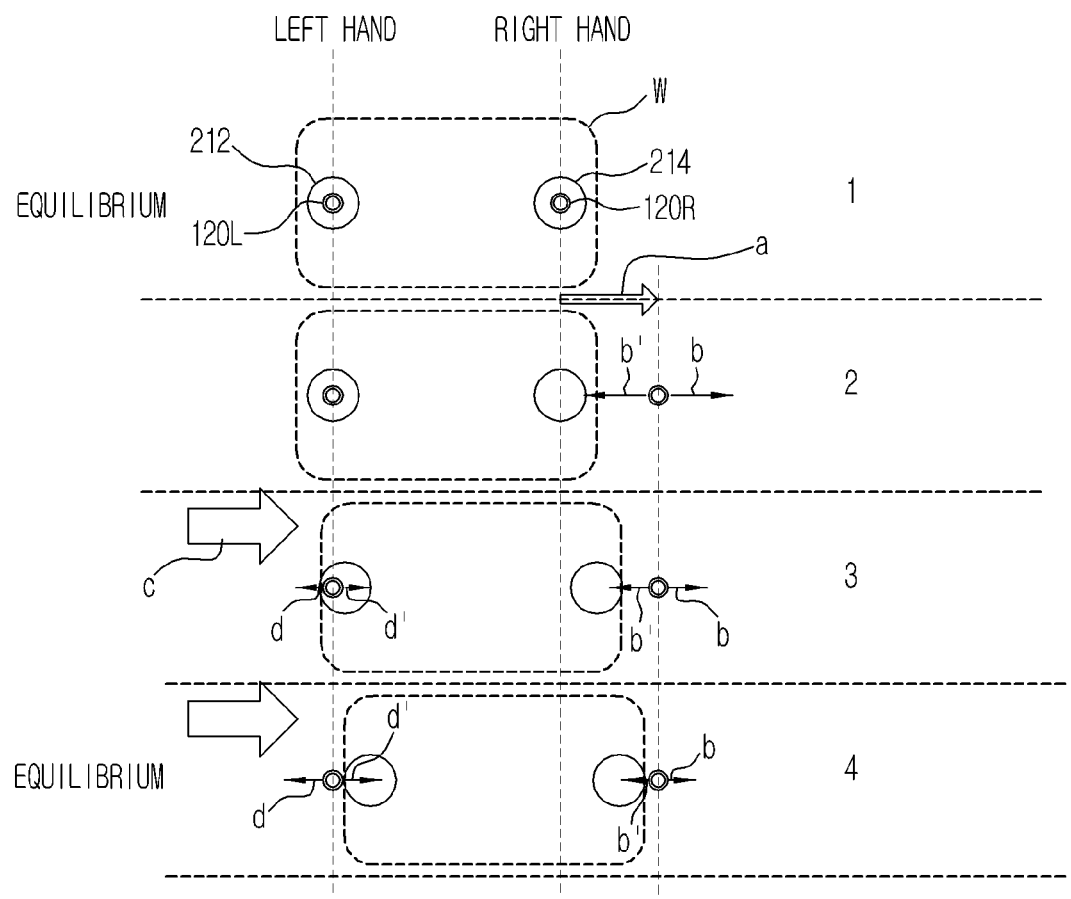
FIG. 13 illustrates an example of changing a working space according to a parallel motion of the guide tube.

FIG. 13 illustrates an example in which the working space W for the surgical instruments 212 and 214 is moved in parallel due to a parallel motion of the guide tube 210, and FIG. 14 illustrates an example in which the working space W for the surgical instruments 212 and 214 is rotated and moved due to a rotational motion of the guide tube 210.

Referring to FIG. 13, in situation 1, each of the first handle unit 120L and the second handle unit 120R is not manipulated by the manipulator and each of the first surgical instrument 212 and the second surgical instrument 214 is close to the boundary surface of the working space W.

In situation 2, the manipulator manipulates the second handle unit 120R in an arrow direction a so as to move the second surgical instrument 214 out of the working space W, therefore, a feedback force b' is generated in the second handle unit 120R in a direction in which a force b applied by the manipulator is offset.

In situation 3, a guide tube (not shown) is moved to an arrow direction c so as to move the second surgical instrument 214 to a target position. Accordingly, the second surgical instrument 214 may be moved to a direction of the target position. As the second surgical instrument 214 is moved, due to a limitation in a distance between the second surgical instrument 214 and the first surgical instrument 212, a feedback force d' to move along a motion direction of the second surgical instrument 214 is generated in the first handle unit 120L for controlling the first surgical instrument 212, and the manipulator applies a force d corresponding to the above-described force d' to the first handle unit 120L so that the first surgical instrument 212 may be maintained in a current state.

A maximum distance between the first surgical instrument 212 and the second surgical instrument 214 exists. That is, there is a limitation in a distance between the first surgical instrument 212 and the second surgical instrument 214 diverged from the guide tube (not shown). For example, in FIG. 13, it will be understood that the first surgical instrument 212 and the second surgical instrument 214 that are close to the boundary surface of the working space W are spaced apart from each other by a maximum distance.

Thus, as the second surgical instrument 214 is moved to the target position, as described above, since the first surgical instrument 212 cannot be spaced apart from the second surgical instrument 214 any more, the first surgical instrument 212 intends to be moved to the direction of the second surgical instrument 214. Also, a feedback force corresponding to the first handle unit 120L may be generated.

In situation 4, however, even when the guide tube (not shown) is moved, the working space W including both the first surgical instrument 212 and the second surgical instrument 214 may not exist. In this case, the guide tube (not shown) may be moved so that the first surgical instrument 212 and the second surgical instrument 214 may have the working space W in which the sum of a vector of the feedback force b' generated in the first handle unit 120L and a vector of the feedback force d' generated in the second handle unit 120R is minimized.

Referring to FIG. 14, in state 1, the first handle unit 120L and the second handle unit 120R are not manipulated by the manipulator and each of the first surgical instrument 212 and the second surgical instrument 214 is close to the boundary surface of the working space W.

In situation 2, the manipulator applies a force to the second handle unit 120R in an arrow direction b so as to move the second surgical instrument 214 out of the working space W. Therefore, the second handle unit 120R may generate a feedback force b' in a direction in which a force b applied by the manipulator is offset. The guide tube 210 may rotate in an arrow direction c so that the working space W may be rotated, as indicated in situation 3.

The transmitting unit 290 may operate by pairing with the receiving unit 195 of the master device 100. The transmitting unit 290 may transmit the second operation control signals scaled by the scaling unit 245 at the enlargement ratio and the image data obtained by the image obtaining unit 230 to the master device 100.

An example of the configuration of the surgical robot system illustrated in FIG. 1 has been described with reference to FIG. 7. The master device 100 may include the scaling unit 135 for scaling the first operation control signals at the reduction ratio, and the slave device 200 may include the scaling unit 245 for scaling the second operation control signals at the enlargement ratio. However, example embodiments are not limited thereto. For example, the master device 100 may include a reduction scaling unit for scaling the first operation control signals at a reduction ratio and an enlargement scaling unit for scaling the second operation control signals at an enlargement ratio, or conversely, the slave device 200 may include both the reduction scaling unit and the enlargement scaling unit, or the master device 100 may include an enlargement scaling unit for scaling the second operation control signals at an enlargement ratio, and the slave device 200 may include a reduction scaling unit for scaling the first operation control signals at a reduction ratio.

The surgical robot system illustrated in FIG. 1 may perform operations of the surgical instruments 212 and 214 while obtaining the working space W when the manipulator operates the surgical instruments 212 and 214 are interlocked out of the range of the current working space W. In this case, in spite of the interlocking of the guide tube 210, when no working space including both target positions of a plurality of surgical instruments exists, a force is generated in a handle unit held by the manipulator so that the manipulator may perceive this state. Subsequently, the manipulator may manipulate one or more of the handle units in a direction in which a force generated in the handle units is offset, so that a part of the plurality of surgical instruments may be firstly moved to the target position.

Hereinafter, a method of controlling the surgical robot system of FIG. 1, in accordance with example embodiments will be described with reference to the drawings.

Figure 8:
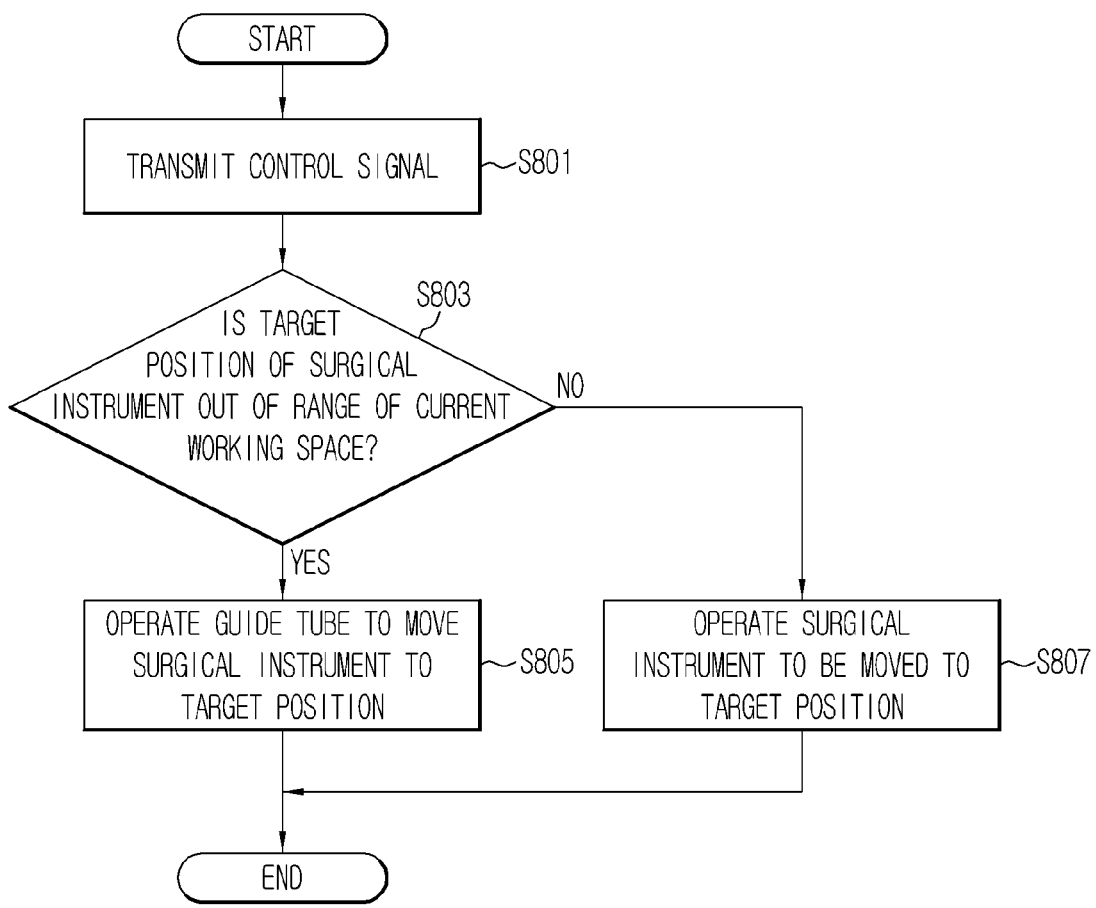
FIG. 8 is a flowchart of a method of controlling a surgical robot system, in accordance with an example embodiment.
Figure 9:
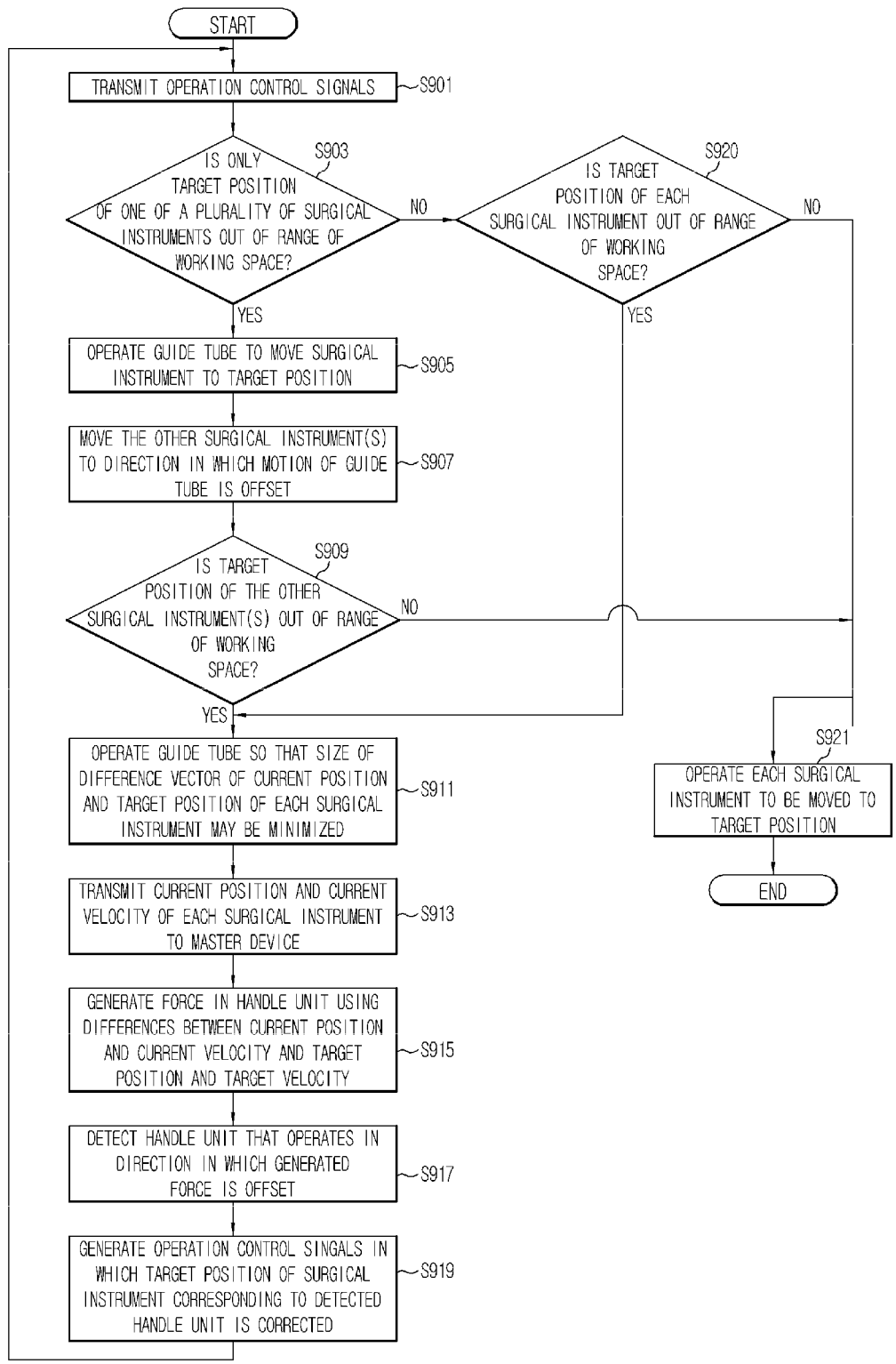
FIG. 9 is a flowchart of a method of controlling a surgical robot system, in accordance with another example embodiment.

FIG. 8 is a flowchart of a method of controlling a surgical robot system in accordance with an example embodiment, and FIG. 9 is a flowchart of a method of controlling a surgical robot system, in accordance with another example embodiment.

Controlling a Single Surgical Instrument

Referring to FIGS. 7 and 8, the slave device 200 may include one surgical instrument and the method of controlling the surgical robot system may include transmitting control signals to the slave device 200 using the master device 100 (S801). Here, the 'control signals' may be first operation control signals generated by the control signal generation unit 140 of the mater device 100. The first operation control signals may be signals generated using the position and velocity of each joint of the handle units 120L and 120R detected by the position detection unit 122 and the velocity detection unit 124 disposed at each joint of the handle units 120L and 120R. Therefore, the first operation control signals indicate the motion of the handle units 120L and 120R that is to be emulated by the surgical instrument.

The slave controller 260 of the slave device 200 may determine whether a target position of the surgical instrument included in the first operation control signals transmitted from the master device 100 is out of the range of the current working space W for the surgical instrument (S803). As a result of determination, if it is determined that the target position corresponds to a position out of the current working space W, the slave controller 260 provides the first operation control signals to the second driving unit 275 so as to operate the guide tube 210 and to move the surgical instrument to the target position (S805). If it is determined that the target position does not correspond to the position out of the current working space W, the slave controller 260 provides the first operation control signals to the first driving unit 270 to directly move the surgical instrument to the target position (S807).

Controlling a plurality of surgical instruments Referring to FIGS. 7 and 9, the slave device 200 may include a plurality of surgical instruments. In this way, when the slave device 200 includes the plurality of surgical instruments, a distance between the plurality of surgical instruments coupled to the guide tube 210 may be limited and thus, operations of the plurality of surgical instruments may be limited. In such a case, as illustrated in FIG. 9, a method of controlling the surgical robot system may include transmitting first operation control signals to the slave device 200 using the master device 100 (S901).

The slave controller 260 of the slave device 200 may determine whether a target position of one of the plurality of surgical instruments is out of the range of the current working space W for the surgical instrument (S903). The target position may be communicated in the first operation control signals transmitted from the master device 100. While FIG. 4 illustrates that the plurality of surgical instruments include the first surgical instrument 212 and the second surgical instrument 214, example embodiments are not limited thereto, and the number of surgical instruments may be greater.

If it is determined, in operation S903, that only the target position of one (the first surgical instrument 212) of the first surgical instrument 212 and the second surgical instrument 214 corresponds to a position out of the current working space W, the slave controller 260 provides the first operation control signals to the second driving unit 275 so as to operate the guide tube 210 and to move the first surgical instrument 212 to the target position (S905). The slave controller 260 of the slave device 200 also provides the first operation control signals to the first driving unit 270 of the second surgical instrument 214 so as to move the second surgical instrument 214 to a direction in which the motion of the guide tube 210 is offset (S907).

Next, the slave controller 260 determines whether the target position of the operating second surgical instrument 214 e.g. corresponds to the position out of the range of the working space W changed according to the motion of the guide tube 210 while the second surgical instrument 214 is moved in the direction in which the motion of the guide tube 210 is offset (S909).

If it is determined, in operation S909, that the target position of the second surgical instrument 214 corresponds to the position out of the range of the changed working space W, the slave controller 260 operates the guide tube 210 so that the size of a difference vector of the current position and the target position of each of the first surgical instrument 212 and the second surgical instrument 214 may be minimized (S911). The slave controller 260 detects the current position and the current velocity of each of the first surgical instrument 212 and the second surgical instrument 214 and transmits the detected current position and current velocity to the master device 100 (S913).

The master controller 160 generates a first compensation control signal for comparing the current position and the current velocity of each of the first surgical instrument 212 and the second surgical instrument 214 with the target position and the target velocity and for compensating for a difference therebetween. Subsequently, the master controller 160 provides the first compensation control signal to the driving unit 170 and generates a force in a direction in which the first handle unit 120L and the second handle unit 120R follow motions of the first surgical instrument 212 and the second surgical instrument 214 (S915).

Next, the master controller 160 detects one of the first handle unit 120L and the second handle unit 120R that operates in a direction in which the generated force is offset (S917), detects position and velocity of each joint of all handle units including the operating handle unit, generates first operation control signals in which the target position of the surgical instrument corresponding to the operating handle unit is changed, using the detected position and velocity (S919), and transmits the generated first operation control signals to the slave device 200 (S901).

Next, using the first operation control signals, the slave controller 260 determines whether only the target position of one surgical instrument between the target position of the first surgical instrument 212 and the target position of the second surgical instrument 214 corresponds to the position out of the range of the working space W (S903). When there is one surgical instrument having the target position corresponding to the position out of the range of the working space W, the method may perform sequentially from Operation S905.

However, if it is determined, in operation S903, that more than one surgical instrument has a target position that is out of the range of the working space W, the slave controller 260 determines whether all of target positions of all surgical instruments, e.g., the target position of the first surgical instrument 212 and the target position of the second surgical instrument 214 are out of the range of the working space W (S920). As a result of determination, if it is determined that all of the target positions are out of the range of the working space W, the method may perform sequentially from Operation S911.

Also, if it is determined, in operation S920, that all of the target positions are not out of the range of the working space W, the slave controller 260 may provide the first operation control signals to the first driving unit 270 indicating not to move the guide tube 210 and to operate only the first surgical instrument 212 and the second surgical instrument 214 to the target position (S921).

As above, example embodiments have been described. In the above-described example embodiments, a part of elements of the master device 100 and the slave device 200 may be implemented with a 'module'. The 'module' includes a software element or a hardware element, such as a field programmable gate array (FPGA) or an application specific integrated circuit (ASIC), and the module may perform functions. However, the module is not limited to software or hardware. The module may be configured to be in a storage medium that may address the module or to execute one or more processors.

As an example, the module may include elements, such as software elements, object-oriented software elements, class elements, and task elements, processes, functions, properties, procedures, subroutines, segments for a program code, drivers, firmware, micro-codes, circuits, data, databases, data structures, tables, arrays, and variables. Functions provided by elements and modules may be combined with a small number of elements and modules or may be subdivided into additional elements and modules. Furthermore, the elements and modules may execute one or more central processing units (CPUs) within a device.

Some example embodiments may be embodied through a medium including a computer-readable code/command for controlling at least one processing element of the above-described embodiments, for example, a computer-readable medium. The medium may correspond to a medium/mediums that enable storage and/or transmission of the computer-readable code. The medium may be non-transitory.

The computer-readable code may be recorded in a medium or may be transmitted through the Internet. Examples of the medium include read-only memory (ROM), random-access memory (RAM), CD-ROMs, magnetic tapes, floppy disks, optical data storage devices, and carrier waves such as data transmission through the Internet. The medium may also be a non-transitory computer-readable medium. Since the mediums can also be distributed networks, the computer-readable code can be stored, transmitted, and executed in a distributed fashion. Furthermore, for example, the processing element may include a processor or a computer processor, and the processing element may be distributed and/or included in one device.

Although a few example embodiments have been shown and described, it would be appreciated by those skilled in the art that changes may be made in these embodiments without departing from their principles and spirit, the scope of which is defined in the claims and their equivalents. For example, while certain operations have been described as being performed by the controller associated with the master device 100 or the slave device 200, one of ordinary skill in the art will appreciate that the operations may be divided between the controllers in various manners. For example, the operations discussed as being performed by the controllers may be segmented between controllers of a plurality of master devices 100 and a plurality of slave devices 100. Further, various operations discussed as being performed by the controller the master device 100 may be performed by the controller of the slave device 200, and vice versa.

Additionally, while example embodiments have been described with relation to a surgical robot, one of ordinary skill in the art will appreciate that the example embodiments may be applied to extend the working space of various other robot systems. For example, robotic systems for use various manufacturing industries. Likewise, in such embodiments, the surgical tools described herein as being attached to the guide tube may be replaced with various tools other than surgical tools. For example, tools utilized in various manufacturing industries. Examples of various tools may include hand tools (e.g., a hammer, anvil, chisel, etc.) and electronic tools (e.g., a welder, torch, etc.).

What is claimed is:

1. A surgical robot system comprising:
a slave device including a surgical instrument; and
a master device configured to transmit a control signal to the slave device to control an operation of the surgical instrument, the slave device including,
a guide tube from which the surgical instrument is extended, and
a controller configured to,
operate the surgical instrument in response to the control signal transmitted from the master device, and
operate the guide tube so as to move the surgical instrument to a target position indicated by the control signal, if the target position of the surgical instrument corresponds to a position out of a range of a current working space for the surgical instrument.

2. The surgical robot system of claim 1, wherein the surgical instrument includes plural surgical instruments,
the control signal includes target positions of each of the plurality of surgical instruments, and
if only one of the plurality of target positions corresponds to a position out of a range of a current working space, the controller is configured to operate the guide tube so as to simultaneously,
move the surgical instrument having the target position out of the range of the current working space to the target position, and
move other ones of the plurality of surgical instruments in a direction in which a motion of the guide tube is offset.

3. The surgical robot system of claim 2, wherein, if each target position of the other ones of the plurality of surgical instruments corresponds to a position out of a range of a working space changed by a motion of the guide tube, then
the controller is configured to transmit a current position and a current velocity of each of the other surgical instruments to the master device, and
the master device is configured to,
calculate a difference between the current position and velocity and a target position and velocity of the other ones of the plurality of surgical instruments,
generate, using manipulation units corresponding to each of the other ones of the plurality of surgical instruments, a force using the calculated difference value, and
inform a manipulator of the surgical instruments that each of the other ones of the plurality of surgical instruments is close to a boundary surface of the changed working space.

4. The surgical robot system of claim 3, wherein the master device is configured to,
detect positions and velocities of all of the manipulation units,
generate control signals used to move the plurality of surgical instruments to new target positions included in the range of the changed working space using the detected position and velocity of each manipulation unit, and
transmit the generated control signals to the slave device.

5. The surgical robot system of claim 1, wherein the surgical instrument includes plural surgical instruments, and
the control signal includes a plurality of target positions of the plurality of surgical instruments, and
if all of the plurality of target positions correspond to a position out of a range of a current working space, the controller is configured to operate the guide tube so as to change the current working space into a working space in which all target positions of the plurality of surgical instruments are included.

6. The surgical robot system of claim 5, wherein, the controller is configured to operate the guide tube so that a vector sum of the target position and a current position of each of the plurality of surgical instruments is minimized, if there is no working space in which all target positions of the plurality of surgical instruments are included.

7. The surgical robot system of claim 6, wherein the controller is configured to transmit a current position and a current velocity of each of the plurality of surgical instruments to the master device, and
the master device is configured to,
calculate a difference between the current position and the current velocity of each of the plurality of surgical instruments with the target position and a target velocity of each of the plurality of surgical instruments,
generate, using manipulation units corresponding to each of the other ones of the plurality of surgical instruments, a force corresponding to each of the plurality of surgical instruments using the calculated difference value, and
inform a manipulator of the surgical instruments that each of the plurality of surgical instruments is close to a boundary surface of the changed working space.

8. The surgical robot system of claim 7, wherein the master device is configured to,
detect positions and velocities of all manipulation units including a manipulation unit that operates in a direction that offsets the force,
generate control signals used to move the plurality of surgical instruments to new target positions included in the range of the changed working space, and
transmitting the generated control signals the slave device.

9. The surgical robot system of claim 1, wherein the controller is configured to operate the guide tube when an operation of the surgical instrument is stopped.

10. The surgical robot system of claim 1, wherein, when the controller operates the guide tube, the master device is configured to instruct a manipulation unit to generate a force corresponding to operating a virtual rigid body to control the operation of the surgical instrument.

11. The surgical robot system of claim 10, wherein the virtual rigid body has a pre-set mass, a pre-set inertia moment, a pre-set frictional force, and a pre-set damping force.

12. A method of controlling a surgical robot system, the surgical robot system including a slave device having a guide tube from which a surgical instrument is extended and a master device configured to transmit a control signal to the surgical instrument, the control signal including a target position for the surgical instrument, the method comprising:
determining whether the target position of the surgical instrument corresponds to a position out of a range of a current working space for the surgical instrument; and
operating the guide tube so as to move the surgical instrument to the target position, if the target position corresponds to the position out of the range of the current working space for the surgical instrument.

13. The method of claim 12, wherein, if the surgical robot system includes plural surgical instruments, the determining of whether the target position corresponds to the position out of the range of the current working space includes determining whether the target position puts only one among the plurality of surgical instruments out of the range of the current working space or all of the plurality of surgical instruments out of the range of the current working space.

14. The method of claim 13, wherein, if it is determined that only one among the plurality of surgical instruments has the target position out of the range of the current working space, the method further comprising:
operating the guide tube in a state in which the one surgical instrument is stopped; and
simultaneously moving,
the one surgical instrument to the target position, and
other ones of the surgical instruments in a direction in which a motion of the guide tube is offset.

15. The method of claim 14, wherein, if the target position of other ones of the plurality of surgical instruments corresponds to the position out of the range of the working space changed by the motion of the guide tube, then the method further comprises:
transmitting, to the master device, a current position and a current velocity of each of the other surgical instruments are transmitted to the master device;
calculate a difference between the current position and velocity and a target position and velocity of the other ones of the other surgical instruments,
generating a force in each manipulation unit corresponding to each of the other surgical instruments using the difference, and
informing a manipulator of the surgical instruments that each of the other ones of the plurality of surgical instruments is close to a boundary surface of the changed working space.

16. The method of claim 15, wherein, after the force is generated in each manipulation unit using the difference, the method further includes,
detecting positions and velocities of all manipulation units,
generating control signals used to move the plurality of surgical instruments to new target positions included in the range of the changed working space using the detected position and velocity of each manipulation unit, and
transmitting the generated control signals to the slave device.

17. The method of claim 13, further comprising:
moving the guide tube so as to change the current working space into a working space in which all target positions of the plurality of surgical instruments are included, if the control signal is a signal used to move all of the plurality of surgical instruments to the target position out of the range of the current working space.

18. The method of claim 17, further comprising:
operating the guide tube so that the vector sum of a target position and a current position of each of the plurality of surgical instruments is minimized, if there is no working space in which all target positions of the plurality of surgical instruments are included.

19. The method of claim 18, further comprising:
transmitting, to the master device, a current position and a current velocity of each of the plurality of surgical instruments, and
calculating, by the master device, a difference between the current position and the current velocity of each of the plurality of surgical instruments and a target position and a target velocity of each of the plurality of surgical instruments,
generating a force in each manipulation unit corresponding to each of the plurality of surgical instruments using the calculated difference, and
informing a manipulator of the surgical instruments that each of the plurality of surgical instruments is close to a boundary surface of the changed working space.

20. The method of claim 19, after a force is generated in each manipulation unit using the difference, the method further includes,
detecting positions and velocities of all manipulation units;
generating control signals used to move the plurality of surgical instruments to new target positions included in the range of the changed working space using the detected position and velocity of each manipulation unit, and
transmitting the generated control signals to the slave device.

* * * * *